US006265403B1

(12) United States Patent
Fraley et al.

(10) Patent No.: US 6,265,403 B1
(45) Date of Patent: Jul. 24, 2001

(54) ANGIOGENESIS INHIBITORS

(75) Inventors: Mark E. Fraley, North Wales; Randall W. Hungate, Lansdale; Andrew J. Tebben, Wallingford, all of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/480,717

(22) Filed: Jan. 7, 2000

Related U.S. Application Data

(60) Provisional application No. 60/116,596, filed on Jan. 20, 1999.

(51) Int. Cl.[7] ............... A61K 31/535; C07D 401/04; C07D 413/04
(52) U.S. Cl. .............. 514/235.2; 544/364; 544/124; 546/277.4; 514/253.01; 514/339
(58) Field of Search .............. 544/364, 124; 514/253.01, 235.2, 339; 546/277.4

(56) References Cited

FOREIGN PATENT DOCUMENTS

| 0574618 | * | 6/1992 | (EP) . |
| 643 059 | | 3/1995 | (EP) . |
| 1587692 | * | 3/1970 | (FR) . |
| WO 98/29408 | | 7/1998 | (WO) . |
| WO 00/09495 | | 2/2000 | (WO) . |

OTHER PUBLICATIONS

CAS Printout for Ohkura et al., Jan. 1990.*
CAS Printout for Naito et al., Jan. 1986.*
CAS Printout for AT 332401, Sep. 1976.*
CAS Printout for Kahnt et al., Jan. 1972.*
CAS Printout for FR 1587692, Mar. 1970.*
CAS Printout for Fanshawe et al., Jan. 1970.*
CAS Printout for Carpino et al., Nov. 1996.*
CAS Printout for Amat et al., Jan. 1994.*
CAS Printout for Seki et al., Jan. 1990.*
Burke, T. R., Jr., Stem Cells, vol. 12, pp. 1–6, 1994.
Amirkhosravi, A., et al., Platelets, vol. 10, pp. 285–292, 1999.
Eliceiri, B. P., et al., Molecular Cell, vol. 4, pp. 915–924, 1999.
Gerber, H–P, et al., Nature Medicine, vol. 5(6), pp. 623–628, 1999.
Brower, V., Nature Biotechnology, vol. 17, pp. 963–968, 1999.
Shibuya, M., et al., Oncogene, vol. 5, pp. 519–524, 1990.
Terman, B. I., et al., Oncogene, vol. 6, pp. 1677–1683, 1991.
Ohkura, K., et al., Heterocycles, vol. 31(10), pp. 1833–1836, 1990.
Friderichs, E., et al., Arch. Pharm., vol. 308(9), pp. 663–674, 1975.
Schut, R., et al., Journal of Medicinal Chemistry., vol. 13, pp. 394–397, 1970.

* cited by examiner

*Primary Examiner*—John M. Ford
*Assistant Examiner*—Hong Liu
(74) *Attorney, Agent, or Firm*—J. Antonio Garcia-Rivas; Mark R. Daniel

(57) ABSTRACT

The present invention relates to compounds which inhibit tyrosine kinase enzymes, compositions which contain tyrosine kinase inhibiting compounds and methods of using tyrosine kinase inhibitors to treat tyrosine kinase-dependent diseases and conditions such as angiogenenesis, cancer, atherosclerosis, diabetic retinopathy, and the like in mammals.

4 Claims, No Drawings

ANGIOGENESIS INHIBITORS

RELATED APPLICATIONS

This application claims priority under 35 U.S.C. § 119(e) from U.S. Provisional Application 60/116,596 filed Jan. 20$^{th}$, 1999.

BACKGROUND OF THE INVENTION

The present invention relates to compounds which inhibit tyrosine kinase enzymes, compositions which contain tyrosine kinase inhibiting compounds and methods of using tyrosine kinase inhibitors to treat tyrosine kinase-dependent diseases and conditions such as neoangiogenesis, cancer, tumor growth, atherosclerosis, age related macular degeneration, diabetic retinopathy, inflammatory diseases, and the like in mammals.

Aberrant vascularization is a key component in numerous disease states. For example, vascularization is a critical element of most solid tumors, such as cancers of the brain, genitourinary tract, lymphatic system, stomach, larynx and lung. These include histiocytic lymphoma, lung adenocarcinoma and small cell lung cancers. Additional examples include cancers in which overexpression or activation of Raf-activating oncogenes (e.g., K-ras, erb-B) is observed. More particularly, such cancers include pancreatic and breast carcinoma. Similarly, aberrant vascular growth in the retina can lead to visual degeneration which can culminate in blindness.

Experimental evidence suggests that the growth factor VEGF plays a critical role in angiogenesis. Vascular endothelial growth factor (VEGF) binds the high affinity membrane-spanning tyrosine kinase receptors KDR and Flt-1. Cell culture and gene knockout experiments indicate that each receptor contributes to different aspects of angiogenesis. KDR mediates the mitogenic function of VEGF whereas Flt-1 appears to modulate non-mitogenic functions such as those associated with cellular adhesion. Inhibiting KDR thus modulates the level of mitogenic VEGF activity and would therefore disrupt angiogenesis, providing a treatment for angiogenesis-mediated diseases, such as tumor proliferation, diabetic retinopathy, macular degeneration, inflammation, and the like.

VEGF accounts for most of the angiogenic activity produced in or near the retina in diabetic retinopathy. Ocular VEGF mRNA and protein are elevated by conditions such as retinal vein occlusion in primates and decreased $pO_2$ levels in mice that lead to neovascularization. Intraocular injections of anti-VEGF monoclonal antibodies or VEGF receptor immunofusions inhibit ocular neovascularization in both primate and rodent models. Regardless of the cause of induction of VEGF in human diabetic retinopathy, inhibition of ocular VEGF is useful in treating the disease.

Expression of VEGF is also significantly increased in hypoxic regions of animal and human tumors adjacent to areas of necrosis. VEGF is also upregulated by the expression of the oncogenes ras, raf, src and mutant p53 (all of which are relevant to targeting cancer). Monoclonal anti-VEGF antibodies inhibit the growth of human tumors in nude mice. Although these same tumor cells continue to express VEGF in culture, the antibodies do not diminish their mitotic rate. Thus, tumor-derived VEGF does not function as an autocrine mitogenic factor. Therefore, VEGF contributes to tumor growth in vivo by promoting angiogenesis through its paracrine vascular endothelial cell chemotactic and mitogenic activities. These monoclonal antibodies also inhibit the growth of typically less well vascularized human colon cancers in athymic mice and decrease the number of tumors arising from inoculated cells. Viral expression of a VEGF-binding construct of Flk-1, Flt-1, the mouse KDR receptor homologue, truncated to eliminate the cytoplasmic tyrosine kinase domains but retaining a membrane anchor, virtually abolishes the growth of a transplantable glioblastoma in mice presumably by the dominant negative mechanism of heterodimer formation with membrane spanning endothelial cell VEGF receptors. Embryonic stem cells, which normally grow as solid tumors in nude mice, do not produce detectable tumors if both VEGF alleles are knocked out. Taken together, these data indicate the role of VEGF in the growth of solid tumors.

Known heterocyclic kinase inhibitors are limited due to poor physical properties, pharmacokinetics, and selectivity against related kinases. The compounds of the instant invention represent novel structures which are unique and offer advantages over known KDR kinase inhibitors.

SUMMARY OF THE INVENTION

The present invention relates to compounds of Formula I which inhibit tyrosine kinase enzymes, compositions which contain these tyrosine kinase inhibiting compounds and methods of using the discosed tyrosine kinase inhibitors to treat tyrosine kinase-dependent diseases and conditions such as angiogenenesis, cancer, atherosclerosis, diabetic retinopathy, and the like in mammals.

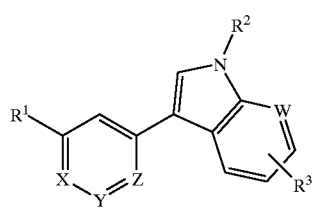

I

DETAILED DESCRIPTION OF THE INVENTION

An embodiment of the present invention is a compound in accordance with formula I:

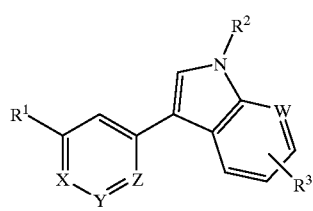

I or a pharmaceutically acceptable salt or hydrate thereof, wherein

W, X, Y and Z are independently CH or N;

R$^1$ is H, C$_{1-10}$ alkyl, C$_{3-6}$ cycloalkyl, aryl, halo, CF$_3$, heterocyclyl, said alkyl, aryl, and heterocyclyl optionally substituted with one to three substituents selected from R$^a$;

R$^2$ is H, C$_{1-6}$ alkyl, aryl, heteroaryl, or C$_{3-6}$ cycloalkyl, said alkyl, aryl, heteroaryl or cycloalkyl optionally substituted with one to three substituents selected from R$^a$;

R$^3$ is H, halo, CN, —C$_{1-6}$ alkylene—CO$_2$R, C$_{1-6}$ alkoxy, —C$_{1-6}$ alkylene-O—C$_{1-6}$ alkyl, C$_{1-6}$ alkyl, aryl, heteroaryl, C$_{3-6}$ cycloalkyl or CO$_2$R, said alkyl, aryl, heteroaryl and cycloalkyl optionally substituted with one to three substituents selected from R$^a$;

R$^a$ is C$_{1-10}$ alkyl, halogen, CF$_3$, NO$_2$, OR, NR$^7$R$^8$, aryl, heterocyclyl, said alkyl, aryl, and heterocyclyl optionally substituted with one or two substituents selected from NO$_2$, CN, halo, aryl, C$_{1-6}$ alkoxy, —C$_{1-6}$ alkylene-O—C$_{1-6}$ alkyl, C$_{1-6}$ alkyl, and CF$_3$;

R is H, or C$_{1-6}$ alkyl; and

R$^7$ and R$^8$ are independently H, C$_{1-10}$ alkyl, C$_{3-6}$ cycloalkyl, COR, —C$_{1-6}$ alkylene-O—C$_{1-6}$ alkyl, C$_{1-6}$ alkoxy, —C$_{1-6}$, alkylene-aryl, COOR, aryl, benzyl, or heterocyclyl, or NR$^7$R$^8$ are taken together to form a 5–10 membered saturated or unsaturated heterocyclic ring containing, in addition to the nitrogen atom attached to R$^7$ and R$^8$, one or two additional heteroatoms selected from N, O, and S, said heterocyclic ring optionally substituted with CN, halo, or C$_{1-6}$ alkyl.

A second embodiment of the present invention is a compound of formula I, wherein W is C—H or N;

X, Y and Z are CH or N, provided only one of X, Y and Z is N;

R$^1$ is H, C$_{1-10}$ alkyl, C$_{3-6}$ cycloalkyl, aryl, halo, CF$_3$, or heterocyclyl, said alkyl, cycloalkyl aryl, and heterocyclyl are optionally substituted with one to three substituents selected from R$^a$;

R$^2$ is H, C$_{1-6}$ alkyl, aryl, heteroaryl, or C$_{3-6}$ cycloalkyl, said alkyl, aryl, heteroaryl and cycloalkyl are optionally substituted with one to three substituents selected from R$^a$;

R$^3$ is H, halo, CN, —C$_{1-6}$ alkylene-CO$_2$R, C$_{1-6}$ alkoxy, —C$_{1-6}$ alkylene-O—C$_{1-6}$ alkyl, C$_{1-6}$ alkyl, aryl, heteroaryl, C$_{3-6}$ cycloalkyl or CO$_2$R, said alkyl, aryl, heteroaryl and cycloalkyl optionally substituted with one to three substituents selected from R$^a$;

R$^a$ is C$_{1-10}$ alkyl, halogen, CF$_3$, NO$_2$, OR, NR$^7$R$^8$, aryl, heterocyclyl, said alkyl, aryl, and heterocyclyl optionally substituted with one or two substituents selected from NO$_2$, CN, halo, aryl, C$_{1-6}$ alkoxy, —C$_{1-6}$ alkylene-O—C$_{1-6}$ alkyl, C$_{1-6}$ alkyl, and CF$_3$;

R is H or C$_{1-6}$ alkyl; and

R$^7$ and R$^8$ are independently H, C$_{1-10}$ alkyl, C$_{3-6}$ cycloalkyl, COR, —C$_{1-6}$ alkylene-O—C$_{1-6}$ alkyl, C$_{1-6}$ alkoxy, —C$_{1-6}$ alkylene-aryl, COOR, aryl, benzyl, C$_{3-10}$ heterocyclyl, or heteroaryl, or NR$^7$R$^8$ are taken together to form a 5–10 membered saturated or unsaturated heterocyclic ring containing, in addition to the nitrogen atom attached to R$^7$ and R$^8$, one or two additional heteroatoms selected from N, O, and S, said heterocyclic ring optionally substituted with CN, halo, or C$_{1-6}$ alkyl.

Another embodiment of the invention is the compound described immediately above wherein Y is N, X is C—H, and Z is C—H.

In yet another embodiment, the compound of Formula I is further defined such that W is C—H.

Still another embodiment further defines the compound of Formula I so that R$^1$ is aryl or heteroaryl, optionally substituted with one, two or three substituents selected from R$^a$.

A further embodiment of the invention is illustrated by the compound as described immediately above but R$^2$ is further defined as C$_{1-6}$ alkyl, optionally substituted with one, two or three substituents selected from R$^a$.

And yet another embodiment is the compound described above wherein R$^a$ is further defined as C$_{1-10}$ alkyl, NR$^7$R$^8$, aryl, or heterocyclyl, said alkyl, aryl, and heterocyclyl optionally substituted with one or two substituents selected from CN, halo, aryl, C$_{1-6}$ alkoxy, —C$_{1-6}$ alkylene-O—C$_{1-6}$ alkyl, and C$_{1-6}$ alkyl.

Still another embodiment is a compound of Formula I, wherein:

W, X, and Z are C—H;

Y is N;

R$^1$ is aryl or heteroaryl, said aryl and heteroaryl optionally substituted with R$^a$;

R$^2$ is H or C$_{1-6}$ alkyl, said alkyl optionally substituted with one, two or three substituents selected from R$^a$; and R$^3$ is H, halo, CO$_2$R, OR or C$_{1-6}$ alkyl.

Another embodiment of the invention is a compound selected from a group consisting of:

3-(5-thiophen-3-yl-pyridin-3-yl)-indole;

1-(2-morpholin-4-yl-ethyl)-3-(5-thiophen-3-yl-pyridin-3-yl)-indole;

1-(2-piperidin-1-yl-ethyl)-3-(5-thiophen-3-yl-pyridin-3-yl)-indole;

1-(3-piperidin-1-yl-propyl)-3-(5-thiophen-3-yl-pyridin-3-yl)-indole;

dimethyl-{3-[3-(5-thiophen-3-yl-pyridin-3-yl)-indol-1-yl]-propyl}-amine;

dimethyl-{2-[3-(5-thiophen-3-yl-pyridin-3-yl)-indol-1-yl]-ethyl}-amine;

1-(1-methyl-piperidin-3-ylmethyl)-3-(5-thiophen-3-yl-pyridin-3-yl)-indole;

1-[3-(4-methyl-piperazin-1-yl)-propyl]-3-(5-thiophen-3-yl-pyridin-3-yl)-indole;

benzyl-(2-methoxy-ethyl)-{2-[3-(5-thiophen-3-yl-pyridin-3-yl)-indol-1-yl]-ethyl}-amine;

1-(2-azepan-1-yl-ethyl)-3-(5-thiophen-3-yl-pyridin-3-yl)-indole;

diethyl-{2-[3-(5-thiophen-3-yl-pyridin-3-yl)-indol-1-yl]-ethyl}-amine;

benzyl-ethyl-{2-[3-(5-thiophen-3-yl-pyridin-3-yl)-indol-1-yl]-ethyl}-amine;

dimethyl-{2-[3-(5-thiophen-3-yl-pyridin-3-yl)-indol-1-yl]-propyl}-amine;

diisopropyl-{2-[3-(5-thiophen-3-yl-pyridin-3-yl)-indol-1-yl]-ethyl}-amine;

dimethyl-{2-methyl-3-[3-(5-thiophen-3-yl-pyridin-3-yl)-indol-1-yl]-propyl)}-amine;

benzyl-methyl-{2-[3-(5-thiophen-3-yl-pyridin-3-yl)-indol-1-yl]-ethyl}-amine;

1-{2-[3-(5-thiophen-3-yl-pyridin-3-yl)-indol-1-yl]-ethyl}-piperidine-4-carbonitrile;

5-methoxy-3-(5-thiophen-3-yl-pyridin-3-yl)-indole;

5-methoxy-1-(2-morpholin-4-yl-ethyl)-3-(5-thiophen-3-yl-pyridin-3-yl)-indole;

5-methoxy-1-(2-piperidin-1-yl-ethyl)-3-(5-thiophen-3-yl-pyridin-3-yl)-indole;

5-methoxy-1-(3-piperidin-1-yl-propyl)-3-(5-thiophen-3-yl-pyridin-3-yl)-indole;

dimethyl-{5-methoxy-3-[3-(5-thiophen-3-yl-pyridin-3-yl)-indol-1-yl]-propyl}-amine;

5-methoxy-1-(1-methyl-piperidin-3-ylmethyl)-3-(5-thiophen-3-yl-pyridin-3-yl)-indole;

5-methoxy-1-[3-(4-methyl-piperazin-1-yl)-propyl]-3-(5-thiophen-3-yl-pyridin-3-yl)-indole;

dimethyl-{2-[5-methoxy-3-(5-thiophen-3-yl-pyridin-3-yl)-indol-1-yl]-propyl}-amine;

dimethyl-{2-methyl-3-[5-methoxy-3-(5-thiophen-3-yl-pyridin-3-yl)-indol-1-yl]-propyl}-amine;

1-{2-[5-methoxy-3-(5-thiophen-3-yl-pyridin-3-yl)-indol-1-yl]-ethyl}-piperidine-4-carbonitrile;

4-chloro-3-(5-thiophen-3-yl-pyridin-3-yl)-indole;

4-chloro-1-(2-morpholin-4-yl-ethyl)-3-(5-thiophen-3-yl-pyridin-3-yl)-indole;

4-chloro-1-(2-piperidin-1-yl-ethyl)-3-(5-thiophen-3-yl-pyridin-3-yl)-indole;

4-chloro-1-(3-piperidin-1-yl-propyl)-3-(5-thiophen-3-yl-pyridin-3-yl)-indole;

dimethyl-{4-chloro-3-[3-(5-thiophen-3-yl-pyridin-3-yl)-indol-1-yl]-propyl}-amine;

4-chloro-1-(1-methyl-piperidin-3-ylmethyl)-3-(5-thiophen-3-yl-pyridin-3-yl)-indole;

4-chloro-1-[3-(4-methyl-piperazin-1-yl)-propyl]-3-(5-thiophen-3-yl-pyridin-3-yl)-indole;

dimethyl-{2-[4-chloro-3-(5-thiophen-3-yl-pyridin-3-yl)-indol-1-yl]-propyl}-amine;

dimethyl-{2-methyl-3-[4-chloro-3-(5-thiophen-3-yl-pyridin-3-yl)-indol-1-yl]-propyl}-amine;

1-{2-[4-chloro-3-(5-thiophen-3-yl-pyridin-3-yl)-indol-1-yl]-ethyl}-piperidine-4-carbonitrile;

5-chloro-3-(5-thiophen-3-yl-pyridin-3-yl)-indole;

5-chloro-1-(2-morpholin-4-yl-ethyl)-3-(5-thophen-3-yl-pyridin-3-yl)-indole;

5-chloro-1-(2-piperidin-1-yl-ethyl)-3-(5-thiophen-3-yl-pyridin-3-yl)-indole;

5-chloro-1-(3-piperidin-1-yl-propyl)-3-(5-thiophen-3-yl-pyridin-3-yl)-indole;

dimethyl-{4-chloro-3-[3-(5-thiophen-3-yl-pyridin-3-yl)-indol-1-yl]-propyl}-amine;

5-chloro-1-(1-methyl-piperidin-3-ylmethyl)-3-(5-thiophen-3-yl-pyridin-3-yl)-indole;

5-chloro-1-[3-(4-methyl-piperazin-1-yl)-propyl]-3-(5-thiophen-3-yl-pyridin-3-yl)-indole;

dimethyl-{2-[5-chloro-3-(5-thiophen-3-yl-pyridin-3-yl)-indol-1-yl]-propyl}-amine;

dimethyl-{2-methyl-3-[5-chloro-3-(5-thiophen-3-yl-pyridin-3-yl)-indol-1-yl]-propyl}-amine;

1-{2-[5-chloro-3-(5-thiophen-3-yl-pyridin-3-yl)-indol-1-yl]-ethyl}-piperidine-4-carbonitrile;

7-methoxy-3-(5-thiophen-3-yl-pyridin-3-yl)-indole;

7-methoxy-1-(2-morpholin-4-yl-ethyl)-3-(5-thiophen-3-yl-pyridin-3-yl)-indole;

7-methoxy-1-(2-piperidin-1-yl-ethyl)-3-(5-thiophen-3-yl-pyridin-3-yl)-indole;

7-methoxy-1-(3-piperidin-1-yl-propyl)-3-(5-thiophen-3-yl-pyridin-3-yl)-indole;

dimethyl-{7-methoxy-3-[3-(5-thiophen-3-yl-pyridin-3-yl)-indol-1-yl]-propyl}-amine;

7-methoxy-1-(1-methyl-piperidin-3-ylmethyl)-3-(5-thiophen-3-yl-pyridin-3-yl)-indole;

7-methoxy-1-[3-(4-methyl-piperazin-1-yl)-propyl]-3-(5-thiophen-3-yl-pyridin-3-yl)-indole;

dimethyl-{2-[7-methoxy-3-(5-thiophen-3-yl-pyridin-3-yl)-indol-1-yl]-propyl}-amine;

dimethyl-{2-methyl-3-[7-methoxy-3-(5-thiophen-3-yl-pyridin-3-yl)-indol-1-yl]-propyl}-amine;

1-{2-[7-methoxy-3-(5-thiophen-3-yl-pyridin-3-yl)-indol-1-yl]-ethyl}-piperidine-4-carbonitrile;

6-chloro-3-(5-thiophen-3-yl-pyridin-3-yl)-indole;

6-chloro-1-(2-morpholin-4-yl-ethyl)-3-(5-thiophen-3-yl-pyridin-3-yl)-indole;

6-chloro-1-(2-piperidin-1-yl-ethyl)-3-(5-thiophen-3-yl-pyridin-3-yl)-indole;

6-chloro-1-(3-piperidin-1-yl-propyl)-3-(5-thiophen-3-yl-pyridin-3-yl)-indole;

dimethyl-{6-chloro-3-[3-(5-thiophen-3-yl-pyridin-3-yl)-indol-1-yl]-propyl}-amine;

6-chloro-1-(1-methyl-piperidin-3-ylmethyl)-3-(5-thiophen-3-yl-pyridin-3-yl)-indole;

6-chloro-1-[3-(4-methyl-piperazin-1-yl)-propyl]-3-(5-thiophen-3-yl-pyridin-3-yl)-indole;

dimethyl-{2-[6-chloro-3-(5-thiophen-3-yl-pyridin-3-yl)-indol-1-yl]-propyl}-amine;

dimethyl-{2-methyl-3-[6-chloro-3-(5-thiophen-3-yl-pyridin-3-yl)-indol-1-yl]-propyl}-amine;

1-{2-[6-chloro-3-(5-thiophen-3-yl-pyridin-3-yl)-indol-1-yl]-ethyl}-piperidine-4-carbonitrile;

3-(5-thiophen-3-yl-pyridin-3-yl)-indole-5-carbonitrile;

1-(2-morpholin-4-yl-ethyl)-3-(5-thiophen-3-yl-pyridin-3-yl)-indole-5-carbonitrile;

1-(2-piperidin-1-yl-ethyl)-3-(5-thiophen-3-yl-pyridin-3-yl)-indole-5-carbonitrile;

1-(3-piperidin-1-yl-propyl)-3-(5-thiophen-3-yl-pyridin-3-yl)-indole-5-carbonitrile;

1-(3-dimethylamino-propyl)-3-(5-thiophen-3-yl-pyridin-3-yl)-indole-5-carbonitrile;

1-(1-methyl-piperidin-3-ylmethyl)-3-(5-thiophen-3-yl-pyridin-3-yl)-indole-5-carbonitrile;

1-[3-(4-methyl-piperazin-1-yl)-propyl]-3-(5-thiophen-3-yl-pyridin-3-yl)-indole-5-carbonitrile;

1-(2-dimethylamino-propyl)-3-(5-thiophen-3-yl-pyridin-3-yl)-indole-5-carbonitrile;

1-(1-dimethylamino-2-methyl-propyl)-3-(5-thiophen-3-yl-pyridin-3-yl)-indole-5-carbonitrile;

1-[2-(4-cyano-piperidin-1-yl)-ethyl]-3-(5-thiophen-3-yl-pyridin-3-yl)-indole-5-carbonitrile;

3-(5-thiophen-3-yl-pyridin-3-yl)-indole-4-carboxylic acid methyl ester;

1-(2-morpholin-4-yl-ethyl)-3-(5-thiophen-3-yl-pyridin-3-yl)-indole-4-carboxylic acid methyl ester;

1-(2-piperidin-1-yl-ethyl)-3-(5-thiophen-3-yl-pyridin-3-yl)-indole-4-carboxylic acid methyl ester;

1-(3-piperidin-1-yl-propyl)-3-(5-thiophen-3-yl-pyridin-3-yl)-indole-4-carboxylic acid methyl ester;

1-(3-dimethylamino-propyl)-3-(5-thiophen-3-yl-pyridin-3-yl)-indole-4-carboxylic acid methyl ester;

1-(1-methyl-piperidin-3-ylmethyl)-3-(5-thiophen-3-yl-pyridin-3-yl)-indole-4-carboxylic acid methyl ester;

1-[3-(4-methyl-piperazin-1-yl)-propyl)-3-(5-thiophen-3-yl-pyridin-3-yl)-indole-4-carboxylic acid methyl ester
1-(2-dimethylamino-propyl)-3-(5-thiophen-3-yl-pyridin-3-yl)-indole-4-carboxylic acid methyl ester;
1-(1-dimethylamino-2-methyl-propyl)-3-(5-thiophen-3-yl-pyridin-3-yl)-indole-4-carboxylic acid methyl ester;
1-[2-(4-cyano-piperidin-1-yl-ethyl]-3-(5-thiophen-3-yl-pyridin-3-yl)-indole-4-carboxylic acid methyl ester;
3-(5-thiophen-3-yl-pyridin-3-yl)-pyrrolo[2,3]pyridine;
1-(2-morpholin-4-yl-ethyl)-3-(5-thiophen-3-yl-pyridin-3-yl)-pyrrolo[2,3]pyridine;
1-(2-piperidin-1-yl-ethyl)-3-(5-thiophen-3-yl-pyridin-3-yl)-pyrrolo[2,3]pyridine;
1-(3-piperidin-1-yl-propyl)-3-(5-thiophen-3-yl-pyridin-3-yl)-pyrrolo[2,3]pyridine;
dimethyl-{3-[3-(5-thiophen-3-yl-pyridin-3-yl)-pyrrolo[2,3]pyridin-1-yl]-propyl}-amine;
1-(1-methyl-piperidin-3-ylmethyl)-3-(5-thiophen-3-yl-pyridin-3-yl)-pyrrolo[2,3]pyridine;
1-[3-(4-methyl-piperazin-1-yl)-propyl)-3-(5-thiophen-3-yl-pyridin-3-yl)-pyrrolo[2,3]pyridine;
dimethyl-{2-[3-(5-thiophen-3-yl-pyridin-3-yl-pyrrlo[2,3]pyridin-1-yl]-propyl}-amine;
dimethyl-{2-methyl-3-[3-(5-thiophen-3-yl-pyridin-3-yl)-pyrrolo[2,3]pyridin-1-yl]-propyl}-amine;
1-{2-[3-(5-thiophen-3-yl-pyridin-3-yl)-pyrrolo[2,3]pyridin-1-yl-ethyl}-piperidine-4-carbonitrile;
3-(5-phenyl-pyridin-3-yl)-indole;
1-(2-morpholin-4-yl-ethyl)-3-(5-phenyl-pyridin-3-yl)-indole;
3-(5-phenyl-pyridin-3-yl)-1-(2-piperidin-1-yl-ethyl)-indole;
3-(5-phenyl-pyridin-3-yl)-1-(3-piperidin-1-yl-propyl)-indole;
dimethyl-{3-[3-(5-phenyl-pyridin-3-yl)-indol-1-yl]-propyl}-amine;
1-(1-methyl-piperidin-3-ylmethyl)-3-(5-phenyl-pyridin-3-yl)-indole;
1-[3-(4-methyl-piperazin-1-yl)-propyl)-3-(5-phenyl-pyridin-3-yl)-indole;
dimethyl-{2-[3-(5-phenyl-pyridin-3-yl)-indol-1-yl]-propyl}-amine;
dimethyl-{2-methyl-3-[3-(5-phenyl-pyridin-3-yl)-indol-1-yl]-propyl}-amine;
1{2-[3-(5-phenyl-pyridin-3-yl)-indol-1-yl]-ethyl}-piperidine-4-carbonitrile;
5-methoxy-3-(5-phenyl-pyridin-3-yl)-indole;
5-methoxy-1-(2-morpholin-4-yl-ethyl)-3-(5-phenyl-pyridin-3-yl)-indole;
5-methoxy-3-(5-phenyl-pyridin-3-yl)-1-(2-piperidin-1-yl-ethyl)-indole;
5-methoxy-3-(5-phenyl-pyridin-3-yl)-1-(3-piperidin-1-yl-propyl)-indole;
dimethyl-{5-methoxy-3-[3-(5-phenyl-pyridin-3-yl)-indol-1-yl]-propyl}-amine;
1-(1-methyl-piperidin-3-ylmethyl)-5-methoxy-3-(5-phenyl-pyridin-3-yl)-indole;
1-[3-(4-methyl-piperazin-1-yl)-propyl)-5-methoxy-3-(5-phenyl-pyridin-3-yl)-indole;
dimethyl-{2-[5-methoxy-3-(5-phenyl-pyridin-3-yl)-indol-1-yl]-propyl}-amine;
dimethyl-{2-methyl-3-[5-methoxy-3-(5-phenyl-pyridin-3-yl)-indol-1-yl]-propyl}-amine;
1{2-[5-methoxy-3-(5-phenyl-pyridin-3-yl)-indol-1-yl]-ethyl}-piperidine-4-carbonitrile;
4-chloro-3-(5-phenyl-pyridin-3-yl)-indole;
4-chloro-1-(2-morpholin-4-yl-ethyl)-3-(5-phenyl-pyridin-3-yl)-indole;
4-chloro-3-(5-phenyl-pyridin-3-yl)-1-(2-piperidin-1-yl-ethyl)-indole;
4-chloro-3-(5-phenyl-pyridin-3-yl)-1-(3-piperidin-1-yl-propyl)-indole;
dimethyl-{4-chloro-3-[3-(5-phenyl-pyridin-3-yl)-indol-1-yl]-propyl}-amine;
1-(1-methyl-piperidin-3-ylmethyl)-4-chloro-3-(5-phenyl-pyridin-3-yl)-indole;
1-[3-(4-methyl-piperazin-1-yl)-propyl)-4-chloro-3-(5-phenyl-pyridin-3-yl)-indole;
dimethyl-{2-[4-chloro-3-(5-phenyl-pyridin-3-yl)-indol-1-yl]-propyl}-amine;
dimethyl-{2-methyl-3-[4-chloro-3-(5-phenyl-pyridin-3-yl)-indol-1-yl]-propyl}-amine;
1-{2-[4-chloro-3-(5-phenyl-pyridin-3-yl)-indol-1-yl]-ethyl}-piperidine-4-carbonitrile;
5-chloro-3-(5-phenyl-pyridin-3-yl)-indole;
5-chloro-1-(2-morpholin-4-yl-ethyl)-3-(5-phenyl-pyridin-3-yl)-indole;
5-chloro-3-(5-phenyl-pyridin-3-yl)-1-(2-piperidin-1-yl-ethyl)-indole;
5-chloro-3-(5-phenyl-pyridin-3-yl)-1-(3-piperidin-1-yl-propyl)-indole;
dimethyl-{5-chloro-3-[3-(5-phenyl-pyridin-3-yl)-indol-1-yl]-propyl}-amine;
1-(1-methyl-piperidin-3-ylmethyl)-5-chloro-3-(5-phenyl-pyridin-3-yl)-indole;
1-[3-(4-methyl-piperazin-1-yl)-propyl)-5-chloro-3-(5-phenyl-pyridin-3-yl)-indole;
dimethyl-{2-[5-chloro-3-(5-phenyl-pyridin-3-yl)-indol-1-yl]-propyl}-amine;
dimethyl-{2-methyl-3-[5-chloro-3-(5-phenyl-pyridin-3-yl)-indol-1-yl]-propyl}-amine;
1-{2-[5-chloro-3-(5-phenyl-pyridin-3-yl)-indol-1-yl]-ethyl}-piperidine-4-carbonitrile;
7-methoxy-3-(5-phenyl-pyridin-3-yl)-indole;
7-methoxy-1-(2-morpholin-4-yl-ethyl)-3-(5-phenyl-pyridin-3-yl)-indole;
7-methoxy-3-(5-phenyl-pyridin-3-yl)-1-(2-piperidin-1-yl-ethyl)-indole;
7-methoxy-3-(5-phenyl-pyridin-3-yl)-1-(3-piperidin-1-yl-propyl)-indole;
dimethyl-{7-methoxy-3-[3-(5-phenyl-pyridin-3-yl)-indol-1-yl]-propyl}-amine;
1-(1-methyl-piperldin-3-ylmethyl)-7-methoxy-3-(5-phenyl-pyridin-3-yl)-indole;
1-[3-(4-methyl-piperazin-1-yl)-propyl)-7-methoxy-3-(5-phenyl-pyridin-3-yl)-indole;
dimethyl-{2-[7-methoxy-3-(5-phenyl-pyridin-3-yl)-indol-1-yl]-propyl}-amine;
dimethyl-{2-methyl-3-[7-methoxy-3-(5-phenyl-pyridin-3-yl)-indol-1-yl]-propyl}-amine;
1-{2-[7-methoxy-3-(5-phenyl-pyridin-3-yl)-indol-1-yl]-ethyl}-piperidine-4-carbonitrile;

6-chloro-3-(5-phenyl-pyridin-3-yl)-indole;
6-chloro-1-(2-morpholin-4-yl-ethyl)-3-(5-phenyl-pyridin-3-yl)-indole;
6-chloro-3-(5-phenyl-pyridin-3-yl)-1-(2-piperidin-1-yl-ethyl)-indole;
6-chloro-3-(5-phenyl-pyridin-3-yl)-1-(3-piperidin-1-yl-propyl)-indole;
dimethyl-{6-chloro-3-[3-(5-phenyl-pyridin-3-yl)-indol-1-yl]-propyl}-amine;
1-(1-methyl-piperidin-3-ylmethyl)-6-chloro-3-(5-phenyl-pyridin-3-yl)-indole;
1-[3-(4-methyl-piperazin-1-yl)-propyl]-6-chloro-3-(5-phenyl-pyridin-3-yl)-indole;
dimethyl-{2-[6-chloro-3-(5-phenyl-pyridin-3-yl)-indol-1-yl]-propyl}-amine;
dimethyl-{2-methyl-3-[6-chloro-3-(5-phenyl-pyridin-3-yl)-indol-1-yl]-propyl}-amine;
1-{2-[6-chloro-3-(5-phenyl-pyridin-3-yl)-indol-1-yl]-ethyl}-piperidine-4-carbonitrile;
3-(5-phenyl-pyridin-3-yl)-indole-5-carbonitrile;
1-(2-morpholin-4-yl-ethyl)-3-(5-phenyl-pyridin-3-yl)-indole-5-carbonitrile;
1-(2-piperidin-1-yl-ethyl)-3-(5-phenyl-pyridin-3-yl)-indole-5-carbonitrile;
1-(3-piperidin-1-yl-propyl)-3-(5-phenyl-pyridin-3-yl)-indole-5-carbonitrile;
1-(3-dimethylamino-propyl)-3-(5-phenyl-pyridin-3-yl)-indole-5-carbonitrile;
1-(1-methyl-piperidin-3-ylmethyl)-3-(5-phenyl-pyridin-3-yl)-indole-5-carbonitrile;
1-[3-(4-methyl-piperazin-1-yl)-propyl]-3-(5-phenyl-pyridin-3-yl)-indole-5-carbonitrile;
1-(2-dimethylamino-propyl)-3-(5-phenyl-pyridin-3-yl)-indole-5-carbonitrile;
1-(1-dimethylamino-2-methyl-propyl)-3-(5-phenyl-pyridin-3-yl)-indole-5-carbonitrile;
1-[2-(4-cyano-piperidin-1-yl-ethyl 1–3-(5-phenyl-pyridin-3-yl)-indole-5-carbonitrile;
3-(5-phenyl-pyridin-3-yl)-indole-4-carboxylic acid methyl ester;
1-(2-morpholin-4-yl-ethyl)-3-(5-phenyl-pyridin-3-yl)-indole-4-carboxylic acid methyl ester;
1-(2-piperidin-1-yl-ethyl)-3-(5-phenyl-pyridin-3-yl)-indole-4-carboxylic acid methyl ester;
1-(3-piperidin-1-yl-propyl)-3-(5-phenyl-pyridin-3-yl)-indole-4-carboxylic acid methyl ester;
1-(3-dimethylamino-propyl)-3-(5-phenyl-pyridin-3-yl)-indole-4-carboxylic acid methyl ester;
1-(1-methyl-piperidin-3-ylmethyl)-3-(5-phenyl-pyridin-3-yl)-indole-4-carboxylic acid methyl ester;
1-[3-(4-methyl-piperazin-1-yl)-propyl]-3-(5-phenyl-pyridin-3-yl)-indole-4-carboxylic acid methyl ester;
1-(2-dimethylamino-propyl)-3-(5-phenyl-pyridin-3-yl)-indole-4-carboxylic acid methyl ester;
1-(1-dimethylamino-2-methyl-propyl)-3-(5-phenyl-pyridin-3-yl)-indole-4-carboxylic acid methyl ester;
1-[2-(4-cyano-piperidin-1-yl-ethyl]-3-(5-phenyl-pyridin-3-yl)-indole-4-carboxylic acid methyl ester;
3-(5-phenyl-pyridin-3-yl)-pyrrolo[2,3]pyridine;
1-(2-morpholin-4-yl-ethyl)-3-(5-phenyl-pyridin-3-yl)-pyrrolo[2,3]pyridine;
1-(2-piperidin-1-yl-ethyl)-3-(5-phenyl-pyridin-3-yl)-pyrrolo[2,3]pyridine;
1-(3-piperidin-1-yl-propyl)-3-(5-phenyl-pyridin-3-yl)-pyrrolo[2,3]pyridine;
dimethyl-{3-[3-(5-phenyl-pyridin-3-yl)- pyrrolo[2,3]pyridin-1-yl]-propyl}-amine;
1-(1-methyl-piperidin-3-ylmethyl)-3-(5-phenyl-pyridin-3-yl)-pyrrolo[2,3]pyridine;
1-[3-(4-methyl-piperazin-1-yl)-propyl)-3-(5-phenyl-pyridin-3-yl)-pyrrolo[2,3]pyridine;
dimethyl-{2-[3-(5-phenyl-pyridin-3-yl)-pyrrolo[2,3]pyridin-1-yl]-propyl}-amine;
dimethyl-{2-methyl-3-[3-(5-phenyl-pyridin-3-yl)-pyrrolo[2,3]pyridin-1-yl]-propyl}-amine;
1-{2-[3-(5-phenyl-pyridin-3-yl)-pyrrolo[2,3]pyridin-1-yl]-ethyl}-piperidine-4-carbonitrile;
3-[5-(3-methoxy-phenyl)-pyridin-3-yl]-indole;
3-[5-(3-methoxy-phenyl)-pyridin-3-yl]-1-(2-morpholin-4-yl-ethyl)-indole;
3-[5-(3-methoxy-phenyl)-pyridin-3-yl]-1-(2-piperidin-1-yl-ethyl)-indole;
3-[5-(3-methoxy-phenyl)-pyridin-3-yl]-1-(3-piperidin-1-yl-propyl)-indole;
dimethyl-{3-[3-(5-(3-methoxy-phenyl)-pyridin-3-yl)-indol-1-yl]-propyl}-amine;
3-[5-(3-methoxy-phenyl)-pyridin-3-yl]-1-(1-methyl-piperidin-3-ylmethyl)-indole;
3-[5-(3-methoxy-phenyl)-pyridin-3-yl]-1-[3-(4-methyl-piperazin-1-yl)-propyl)-indole;
dimethyl-{2-[3-(5-(3-methoxy-phenyl)-1-pyridin-3-yl)-indol-1-yl]-propyl}-amine;
dimethyl-{2-methyl-3-[3-(5-(3-methoxy-phenyl)-pyridin-3-yl)-indol-1-yl]-propyl}-amine;
1-{2-[3-(5-(3-methoxy-phenyl)-pyridin-3-yl)-indol-1-yl]-ethyl}-piperidine-4-carbonitrile;
5-methoxy-3-[5-(3-methoxy-phenyl)-pyridin-3-yl]-indole;
5-methoxy-3-[5-(3-methoxy-phenyl)-pyridin-3-yl]-1-(2-morpholin-4-yl-ethyl)-indole;
5-methoxy-3-[5-(3-methoxy-phenyl)-pyridin-3-yl]-1-(2-piperidin-1-yl-ethyl)-indole;
5-methoxy-3-[5-(3-methoxy-phenyl)-pyridin-3-yl]-1-(3-piperidin-1-yl-propyl)-indole;
dimethyl-{3-[5-methoxy-3-(5-(3-methoxy-phenyl)-pyridin-3-yl)-indol-1-yl]-propyl}-amine;
5-methoxy-3-[5-(3-methoxy-phenyl)-pyridin-3-yl]-1-(1-methyl-piperidin-3-ylmethyl)-indole;
5-methoxy-3-[5-(3-methoxy-phenyl)-pyridin-3-yl]-1-[3-(4-methyl-piperazin-1-yl)-propyl)-indole;
dimethyl-{2-[5-methoxy-3-(5-(3-methoxy-phenyl)-1-pyridin-3-yl)-indol-1-yl]-propyl}-amine;
dimethyl-{2-methyl-3-[5-methoxy-3-(5-(3-methoxy-phenyl)-pyridin-3-yl)-indol-1-yl]-propyl}-amine;
1-{2-[5-methoxy-3-(5-(3-methoxy-phenyl)-pyridin-3-yl)-indol-1-yl]-ethyl}-piperidine-4-carbonitrile;
4-chloro-3-[5-(3-methoxy-phenyl)-pyridin-3-yl]-indole;
4-chloro-3-[5-(3-methoxy-phenyl)-pyridin-3-yl]-1-(2-morpholin-4-yl-ethyl)-indole;
4-chloro-3-[5-(3-methoxy-phenyl)-pyridin-3-yl]-1-(2-piperidin-1-yl-ethyl)-indole;
4-chloro-3-[5-(3-methoxy-phenyl)-pyridin-3-yl]-1-(3-piperidin-1-yl-propyl)-indole;

dimethyl-{3-[4-chloro-3-(5-(3-methoxy-phenyl)-pyridin-3-yl)-indol-1-yl]-propyl}-amine;
4-chloro-3-[5-(3-methoxy-phenyl)-pyridin-3-yl]-1-(1-methyl-piperidin-3-ylmethyl)-indole;
4-chloro-3-[5-(3-methoxy-phenyl)-pyridin-3-yl]-1-[3-(4-methyl-piperazin-1-yl)-propyl)-indole;
dimethyl-{2-[4-chloro-3-(5-(3-methoxy-phenyl)-1-pyridin-3-yl)-indol-1-yl]-propyl}-amine;
dimethyl-{2-methyl-3-[4-chloro-3-(5-(3-methoxy-phenyl)-pyridin-3-yl)-indol-1-yl]-propyl}-amine;
1-{2-[4-chloro-3-(5-(3-methoxy-phenyl)-pyridin-3-yl)-indol-1-yl]-ethyl}-piperidine-4-carbonitrile;
5-chloro-3-[5-(3-methoxy-phenyl)-pyridin-3-yl]-indole;
5-chloro-3-[5-(3-methoxy-phenyl)-pyridin-3-yl]-1-(2-morpholin-4-yl-ethyl)-indole;
5-chloro-3-[5-(3-methoxy-phenyl)-pyridin-3-yl]-1-(2-piperidin-1-yl-ethyl)-indole;
5-chloro-3-[5-(3-methoxy-phenyl)-pyridin-3-yl]-1-(3-piperidin-1-yl-propyl)-indole;
dimethyl-{3-[5-chloro-3-(5-(3-methoxy-phenyl)-pyridin-3-yl)-indol-1-yl]-propyl}-amine;
5-chloro-3-[5-(3-methoxy-phenyl)-pyridin-3-yl]-1-(1-methyl-piperldin-3-ylmethyl)-indole;
5-chloro-3-[5-(3-methoxy-phenyl)-pyridin-3-yl]-1-[3-(4-methyl-piperazin-1-yl)-propyl)-indole;
dimethyl-{2-[5-chloro-3-(5-(3-methoxy-phenyl)-1-pyridin-3-yl)-indol-1-yl]-propyl}-amine;
dimethyl-{2-methyl-3-[5-chloro-3-(5-(3-methoxy-phenyl)-pyridin-3-yl)-indol-1-yl]-propyl}-amine;
1-{2-[5-chloro-3-(5-(3-methoxy-phenyl)-pyridin-3-yl)-indol-1-yl]-ethyl)}-piperidine-4-carbonitrile;
7-methoxy-3-[5-(3-methoxy-phenyl)-pyridin-3-yl]-indole;
7-methoxy-3-[5-(3-methoxy-phenyl)-pyridin-3-yl]-1-(2-morpholin-4-yl-ethyl)-indole;
7-methoxy-3-[5-(3-methoxy-phenyl)-pyridin-3-yl]-1-(2-piperidin-1-yl-ethyl)-indole;
7-methoxy-3-[5-(3-methoxy-phenyl)-pyridin-3-yl]-1-(3-piperidin-1-yl-propyl)-indole;
dimethyl-{3-[7-methoxy-3-(5-(3-methoxy-phenyl)-pyridin-3-yl)-indol-1-yl]-propyl}-amine;
7-methoxy-3-[5-(3-methoxy-phenyl)-pyridin-3-yl]-1-(1-methyl-piperidin-3-ylmethyl)-indole;
7-methoxy-3-[5-(3-methoxy-phenyl)-pyridin-3-yl]-1-[3-(4-methyl-piperazin-1-yl)-propyl)-indole; dimethyl-{2-[7-methoxy-3-(5-(3-methoxy-phenyl)-1-pyridin-3-yl)-indol-1-yl]-propyl}-amine;
dimethyl-{2-methyl-3-[7-methoxy-3-(5-(3-methoxy-phenyl)-pyridin-3-yl)-indol-1-yl]-propyl}-amine;
1-{2-[7-methoxy-3-(5-(3-methoxy-phenyl)-pyridin-3-yl)-indol-1-yl]-ethyl}-piperidine-4-carbonitrile;
6-chloro-3-[5-(3-methoxy-phenyl)-pyridin-3-yl]-indole;
6-chloro-3-[5-(3-methoxy-phenyl)-pyridin-3-yl]-1-(2-morpholin-4-yl-ethyl)-indole;
6-chloro-3-[5-(3-methoxy-phenyl)-pyridin-3-yl]-1-(2-piperidin-1-yl-ethyl)-indole;
6-chloro-3-[5-(3-methoxy-phenyl)-pyridin-3-yl]-1-(3-piperidin-1-yl-propyl)-indole;
dimethyl-{3-[6-chloro-3-(5-(3-methoxy-phenyl)-pyridin-3-yl)-indol1-yl]-propyl}-amine;
6-chloro-3-[5-(3-methoxy-phenyl)-pyridin-3-yl]-1-(1-methyl-piperidin-3-ylmethyl)-indole;
6-chloro-3-[5-(3-methoxy-phenyl)-pyridin-3-yl]-1-[3-(4-methyl-piperazin-1-yl)-propyl)-indole;
dimethyl-{2-[6-chloro-3-(5-(3-methoxy-phenyl)-1-pyridin-3-yl-indol-1-yl]-propyl}-amine;
dimethyl-{2-methyl-3-[6-chloro-3-(5-(3-methoxy-phenyl)-pyridin-3-yl)-indol-1-yl]-propyl}-amine;
1-{2-[6-chloro-3-(5-(3-methoxy-phenyl)-pyridin-3-yl)-indol-1-yl]-ethyl}-piperidine-4-carbonitrile;
3-[5-(3-methoxy-phenyl)-pyridin-3-yl]-indole-5-carbonitrile;
3-[5-(3-methoxy-phenyl)-pyridin-3-yl]-1-(2-morpholin-4-yl-ethyl)-indole-5-carbonitrile;
3-[5-(3-methoxy-phenyl)-pyridin-3-yl]-1-(2-piperidin-1-yl-ethyl)-indole-5-carbonitrile;
3-[5-(3-methoxy-phenyl)-pyridin-3-yl]-1-(3-piperidin-1-yl-propyl)-indole-5-carbonitrile;
1-(3-dimethylamino-propyl)-3-[5-(3-methoxy-phenyl)-pyridin-3-yl]-indole-5-carbonitrile;
3-[5-(3-methoxy-phenyl)-pyridin-3-yl]-1-(1-methyl-piperidin-3-ylmethyl)-indole-5-carbonitrile;
3-[5-(3-methoxy-phenyl)-pyridin-3-yl]-1-[3-(4-methyl-piperazin-1-yl)-propyl)-indole-5-carbonitrile;
1-(2-dimethylamino-propyl)-3-[5-(3-methoxy-phenyl)-pyridin-3-yl]-indole-5-carbonitrile;
1-(1-dimethylamino-2-methyl-propyl)-3-[5-(3-methoxy-phenyl)-pyridin-3-yl]-indole-5-carbonitrile;
1-[2-(4-cyano-piperidin-1-yl-ethyl]-3-[5-(3-methoxy-phenyl)-pyridin-3-yl]-indole-5-carbonitrile;
3-[5-(3-methoxy-phenyl)-pyridin-3-yl]-indole-4-carboxylic acid methyl ester;
3-[5-(3-methoxy-phenyl)-pyridin-3-yl]-1-(2-morpholin-4-yl-ethyl)-indole-4-carboxylic acid methyl ester;
3-[5-(3-methoxy-phenyl)-pyridin-3-yl]-1-(2-piperidin-1-yl-ethyl)-indole-4-carboxylic acid methyl ester;
3-[5-(3-methoxy-phenyl)-pyridin-3-yl]-1-(3-piperidin-1-yl-propyl)-indole-4-carboxylic acid methyl ester;
1-(3-dimethylamino-propyl)-3-[5-(3-methoxy-phenyl)-pyridin-3-yl]-indole-4-carboxylic acid methyl ester;
3-[5-(3-methoxy-phenyl)-pyridin-3-yl]-1-(1-methyl-piperidin-3-ylmethyl)-indole-4-carboxylic acid methyl ester;
3-[5-(3-methoxy-phenyl)-pyridin-3-yl]-1-[3-(4-methyl-piperazin-1-yl)-propyl)-indole-4-carboxylic acid methyl ester;
1-(2-dimethylamino-propyl)-3-[5-(3-methoxy-phenyl)-pyridin-3-yl]-indole-4-carboxylic acid methyl ester;
1-(1-dimethylamino-2-methyl-propyl)-3-[5-(3-methoxy-phenyl)-pyridin-3-yl]-indole-4-carboxylic acid methyl ester;
1-[2-(4-cyano-piperidin-1-yl-ethyl]-3-[5-(3-methoxy-phenyl)-pyridin-3-yl]indole-4-carboxylic acid methyl ester;
3-[5-(3-methoxy-phenyl)-pyridin-3-yl]-pyrrolo[2,3]pyridine;
3-[5-(3-methoxy-phenyl)-pyridin-3-yl]-1-(2-morpholin-4-yl-ethyl)-pyrrolo[2,3]pyridine;
3-[5-(3-methoxy-phenyl)-pyridin-3-yl]-1-(2-piperidin-1-yl-ethyl)-pyrrolo[2,3]pyridine;
3-[5-(3-methoxy-phenyl)-pyridin-3-yl]-1-(3-piperidin-1-yl-propyl)-pyrrolo[2,3]pyridine;
dimethyl-{3-[3-(5-(3-methoxy-phenyl)-pyridin-3-yl)-pyrrolo[2,3]pyridin-1-yl]-propyl}-amine;

3-(3-methoxy-phenyl)-pyridin-3-yl]-1-(1-methyl-piperidin-3-ylmethyl)-pyrrolo[2,3]pyridine;

3-[5-(3-methoxy-phenyl)-pyridin-3-yl]-1-[3-(4-methyl-piperazin-1-yl)-propyl)-pyrrolo[2,3]pyridine;

dimethyl-{2-[3-(5-(3-methoxy-phenyl)-1-pyridin-3-yl)-pyrrolo[2,3]pyridin-1-yl]-propyl}-amine;

dimethyl-{2-methyl-3-[3-(5-(3-methoxy-phenyl)-pyridin-3-yl)-pyrrolo[2,3]pyridin-1-yl]-propyl}-amine;

1-{2-[3-(5-(3-methoxy-phenyl)-pyridin-3-yl)-pyrrolo[2,3]pyridin-1-yl]-ethyl}-piperidine-4-carbonitrile;

3-[5-(4-methoxy-phenyl)-pyridin-3-yl]-indole;

3-[5-(4-methoxy-phenyl)-pyridin-3-yl]-1-(2-morpholin-4-yl-ethyl)-indole;

3-[5-(4-methoxy-phenyl)-pyridin-3-yl]-1-(2-piperidin-1-yl-ethyl)-indole;

3-[5-(4-methoxy-phenyl)-pyridin-3-yl]-1-(3-piperidin-1-yl-propyl)-indole;

dimethyl-{3-[3-(5-(4-methoxy-phenyl)-pyridin-3-yl)-indol-1-yl]-propyl}-amine;

3-[5-(4-methoxy-phenyl)-pyridin-3-yl]-1-(1-methyl-piperidin-3-ylmethyl)-indole;

3-[5-(4-methoxy-phenyl)-pyridin-3-yl]-1-[3-(4-methyl-piperazin-1-yl)-propyl)-indole;

dimethyl-{2-[3-(5-(4-methoxy-phenyl)-1-pyridin-3-yl)-indol-1-yl]-propyl}-amine;

dimethyl-{2-methyl-3-[3-(5-(4-methoxy-phenyl)-pyridin-3-yl)-indol-1-yl]-propyl}-amine;

1-{2-[3-(5-(4-methoxy-phenyl)-pyridin-3-yl)-indol-1-yl]-ethyl}-piperidine-4-carbonitrile;

5-methoxy-3-[5-(4-methoxy-phenyl)-pyridin-3-yl]-1-(2-morpholin-4-yl-ethyl)-indole;

5-methoxy-3-[5-(4-methoxy-phenyl)-pyridin-3-yl]-1-(2-piperidin-1-yl-ethyl)-indole;

5-methoxy-3-[5-(4-methoxy-phenyl)-pyridin-3-yl]-1-(3-piperidin-1-yl-propyl)-indole;

dimethyl-{3-[5-methoxy-3-(5-(4-methoxy-phenyl)-pyridin-3-yl)-indol-1-yl]-propyl}-amine;

5-methoxy-3-[5-(4-methoxy-phenyl)-pyridin-3-yl]-1-(1-methyl-piperidin-3-ylmethyl)-indole;

5-methoxy-3-[5-(4-methoxy-phenyl)-pyridin-3-yl]-1-[3-(4-methyl-piperazin-1-yl)-propyl)-indole;

dimethyl-{2-[5-methoxy-3-(5-(4-methoxy-phenyl)-1-pyridin-3-yl)-indol-1-yl]-propyl}-amine;

dimethyl-{2-methyl-3-[5-methoxy-3-(5-(4-methoxy-phenyl)-pyridin-3-yl)-indol-1-yl]-propyl}-amine;

1-{2-[5-methoxy-3-(5-(4-methoxy-phenyl)-pyridin-3-yl)-indol-1-yl]-ethyl}-piperidine-4-carbonitrile;

4-chloro-3-[5-(4-methoxy-phenyl)-pyridin-3-yl]-indole;

4-chloro-3-[5-(4-methoxy-phenyl)-pyridin-3-yl]-1-(2-morpholin-4-yl-ethyl)-indole;

4-chloro-3-[5-(4-methoxy-phenyl)-pyridin-3-yl]-1-(2-piperidin-1-yl-ethyl)-indole;

4-chloro-3-[5-(4-methoxy-phenyl)-pyridin-3-yl]-1-(3-piperidin-1-yl-propyl)-indole;

dimethyl-{3-[4-chloro-3-(5-(4-methoxy-phenyl)-pyridin-3-yl)-indol-1-yl]-propyl}-amine;

4-chloro-3-[5-(4-methoxy-phenyl)-pyridin-3-yl]-1-(1-methyl-piperidin-3-ylmethyl)-indole;

4-chloro-3-[5-(4-methoxy-phenyl)-pyridin-3-yl]-1-[3-(4-methyl-piperazin-1-yl)-propyl)-indole;

dimethyl-{2-[4-chloro-3-(5-(4-methoxy-phenyl)-1-pyridin-3-yl)-indol-1-yl]-propyl}-amine;

dimethyl-{2-methyl-3-[4-chloro-3-(5-(4-methoxy-phenyl)-pyridin-3-yl)-indol-1-yl]-propyl}-amine;

1-{2-[4-chloro-3-(5-(4-methoxy-phenyl)-pyridin-3-yl)-indol-1-yl]-ethyl}-piperidine-4-carbonitrile;

5-chloro-3-[5-(4-methoxy-phenyl)-pyridin-3-yl]-indole;

5-chloro-3-[5-(4-methoxy-phenyl)-pyridin-3-yl]-1-(2-morpholin-4-yl-ethyl)-indole;

5-chloro-3-[5-(4-methoxy-phenyl)-pyridin-3-yl]-1-(2-piperidin-1-yl-ethyl)-indole;

5-chloro-3-[5-(4-methoxy-phenyl)-pyridin-3-yl]-1-(3-piperidin-1-yl-propyl)-indole;

dimethyl-{3-[5-chloro-3-(5-(4-methoxy-phenyl)-pyridin-3-yl)-indol-1-yl]-propyl)-amine;

5-chloro-3-[5-(4-methoxy-phenyl)-pyridin-3-yl]-1-(1-methyl-piperidin-3-ylmethyl)-indole;

5-chloro-3-[5-(4-methoxy-phenyl)-pyridin-3-yl]-1-[3-(4-methyl-piperazin-1-yl)-propyl)-indole;

dimethyl-{2-[5-chloro-3-(5-(3-methoxy-phenyl)-1-pyridin-3-yl)-indol-1-yl-]1-propyl}-amine;

dimethyl-{2-methyl-3-[5-chloro-3-(5-(4-methoxy-phenyl)-pyridin-3-yl)-indol-1-yl]-propyl}-amine;

1-{2-[5-chloro-3-(5-(4-methoxy-phenyl)-pyridin-3-yl)-indol-1-yl]-ethyl}-piperidine-4-carbonitrile;

7-methoxy-3-[5-(4-methoxy-phenyl)-pyridin-3-yl]-indole;

7-methoxy-3-[5-(4-methoxy-phenyl)-pyridin-3-yl]-1-(2-morpholin-4-yl-ethyl)-indole;

7-methoxy-3-[5-(4-methoxy-phenyl)-pyridin-3-yl]-1-(2-piperidin-1-yl-ethyl)-indole;

7-methoxy-3-[5-(4-methoxy-phenyl)-pyridin-3-yl]-1-(3-piperidin-1-yl-propyl)-indole;

dimethyl-{3-[7-methoxy-3-(5-(4-methoxy-phenyl)-pyridin-3-yl)-indol-1-yl]-propyl}-amine;

7-methoxy-3-[5-(4-methoxy-phenyl)-pyridin-3-yl]-1-(1-methyl-piperidin-3-ylmethyl)-indole;

7-methoxy-3-[5-(4-methoxy-phenyl)-pyridin-3-yl]-1-[3-(4-methyl-piperazin-1-yl)-propyl)-indole;

dimethyl-{2-[7-methoxy-3-(5-(4-methoxy-phenyl)-1-pyridin-3-yl)-indol-1-yl]-propyl}-amine;

dimethyl-{2-methyl-3-[7-methoxy-3-(5-(4-methoxy-phenyl)-pyridin-3-yl)-indol-1-yl]-propyl}-amine;

1-{2-[7-methoxy-3-(5-(4-methoxy-phenyl)-pyridin-3-yl)-indol-1-yl]-ethyl}-piperidine-4-carbonitrile;

6-chloro-3-[5-(4-methoxy-phenyl)-pyridin-3-yl]-indole;

6-chloro-3-[5-(4-methoxy-phenyl)-pyridin-3-yl]-1-(2-morpholin-4-yl-ethyl)-indole;

6-chloro-3-[5-(4-methoxy-phenyl)-pyridin-3-yl]-1-(2-piperidin-1-yl-ethyl)-indole;

6-chloro-3-[5-(4-methoxy-phenyl)-pyridin-3-yl]-1-(3-piperidin-1-yl-propyl)-indole;

dimethyl-{3-[6-chloro-3-(5-(4-methoxy-phenyl)-pyridin-3-yl)-indol-1-yl]-propyl}-amine;

6-chloro-3-[5-(4-methoxy-phenyl)-pyridin-3-yl]-1-(1-methyl-piperidin-3-ylmethyl)-indole;

6-chloro-3-[5-(4-methoxy-phenyl)-pyridin-3-yl]-1-[3-(4-methyl-piperazin-1-yl)-propyl)-indole;

dimethyl-{2-[6-chloro-3-(5-(4-methoxy-phenyl)-1-pyridin-3-yl)-indol-1-yl]-propyl}-amine;

dimethyl-{2-methyl-3-[6-chloro-3-(5-(3-methoxy-phenyl)-pyridin-3-yl)-indol-1-yl]-propyl}-amine;

1-{2-[6-chloro-3-(5-(3-methoxy-phenyl)-pyridin-3-yl)-indol-1-yl]-ethyl}-piperidine-4-carbonitrile;

3-[5-(4-methoxy-phenyl)-pyridin-3-yl]-indole-5-carbonitrile;
3-[5-(3-methoxy-phenyl)-pyridin-3-yl]-1-(2-morpholin-4-yl-ethyl)-indole-5-carbonitrile;
3-[5-(4-methoxy-phenyl)-pyridin-3-yl]-1-(2-piperidin-1-yl-ethyl)-indole-5-carbonitrile;
3-[5-(4-methoxy-phenyl)-pyridin-3-yl]-1-(3-piperidin-1-yl-propyl)-indole-5-carbonitrile;
1-(3-dimethylamino-propyl)-3-[5-(4-methoxy-phenyl)-pyridin-3-yl]-indole-5-carbonitrile;
3-[5-(4-methoxy-phenyl)-pyridin-3-yl]-1-(1-methyl-piperidin-3-ylmethyl)-indole-5-carbonitrile;
3-[5-(4-methoxy-phenyl)-pyridin-3-yl]-1-[3-(4-methyl-piperazin-1-yl)-propyl]-indole-5-carbonitrile;
1-(2-dimethylamino-propyl)-3-[5-(4-methoxy-phenyl)-pyridin-3-yl]-indole-5-carbonitrile;
1-(1-dimethylamino-2-methyl-propyl)-3-[5-(4-methoxy-phenyl)-pyridin-3-yl]-indole-5-carbonitrile;
1-[2-(4-cyano-piperidin-1-yl-ethyl]-3-[5-(4-methoxy-phenyl)-pyridin-3-yl]-indole-5-carbonitrile;
3-[5-(4-methoxy-phenyl)-pyridin-3-yl]-indole-4-carboxylic acid methyl ester;
3-[5-(4-methoxy-phenyl)-pyridin-3-yl]-1-(2-morpholin-4-yl-ethyl)-indole-4-carboxylic acid methyl ester;
3-[5-(4-methoxy-phenyl)-pyridin-3-yl]-1-(2-piperidin-1-yl-ethyl)-indole-4-carboxylic acid methyl ester;
3-[5-(4-methoxy-phenyl)-pyridin-3-yl]-1-(3-piperidin-1-yl-propyl)-indole-4-carboxylic acid methyl ester;
1-(3-dimethylamino-propyl)-3-[5-(4-methoxy-phenyl)-pyridin-3-yl]-indole-4-carboxylic acid methyl ester;
3-[5-(4-methoxy-phenyl)-pyridin-3-yl]-1-(1-methyl-piperidin-3-ylmethyl)-indole-4-carboxylic acid methyl ester;
3-[5-(4-methoxy-phenyl)-pyridin-3-yl]-1-[3-(4-methyl-piperazin-1-yl)-propyl)-indole-4-carboxylic acid methyl ester;
1-(2-dimethylamino-propyl)-3-[5-(4-methoxy-phenyl)-pyridin-3-yl]-indole-4-carboxylic acid methyl ester;
1-(1-dimethylamino-2-methyl-propyl)-3-[5-(4-methoxy-phenyl)-pyridin-3-yl]-indole-4-carboxylic acid methyl ester;
1-[2-(4-cyano-piperidin-1-yl-ethyl]-3-[5-(4-methoxy-phenyl)-pyridin-3-yl]-indole-4-carboxylic acid methyl ester;
3-[5-(4-methoxy-phenyl)-pyridin-3-yl]-pyrrolo[2,3]pyridine;
3-[5-(4-methoxy-phenyl)-pyridin-3-yl]-1-(2-morpholin-4-yl-ethyl)-pyrrolo[2,3]pyridine;
3-[5-(4-methoxy-phenyl)-pyridin-3-yl]-1-(2-piperidin-1-yl-ethyl)-pyrrolo[2,3]pyridine;
3-[5-(4-methoxy-phenyl)-pyridin-3-yl]-1-(3-piperidin-1-yl-propyl)-pyrrolo[2,3]pyridine;
dimethyl-{3-[3-(5-(4-methoxy-phenyl)-pyridin-3-yl)-pyrrolo[2,3]pyridin-1-yl]-propyl}-amine;
3-[5-(4-methoxy-phenyl)-pyridin-3-yl]-1-(1-methyl-piperidin-3-ylmethyl)-pyrrolo[2,3]pyridine;
3-[5-(4-methoxy-phenyl)-pyridin-3-yl]-1-[3-(4-methyl-piperazin-1-yl)-propyl]-pyrrolo[2,3]pyridine;
dimethyl-{2-[3-(5-(4-methoxy-phenyl)-1-pyridin-3-yl)-pyrrolo[2,3]pyridin-1-yl]-propyl}-amine;
dimethyl-{2-methyl-3-[3-(5-(4-methoxy-phenyl)-pyridin-3-yl)-pyrrolo[2,3]pyridin-1-yl]-propyl}-amine;
1-{2-[3-(5-(4-methoxy-phenyl)-pyridin-3-yl)-pyrrolo[2,3]pyridin-1-yl]-ethyl}-piperidine-4-carbonitrile;
3-[5-(3-chloro-phenyl)-pyridin-3-yl1-indole;
3-[5-(3-chloro-phenyl)-pyridin-3-yl]-1-(2-morpholin-4-yl-ethyl)-indole;
3-[5-(3-chloro-phenyl)-pyridin-3-yl]-1-(2-piperidin-1-yl-ethyl)-indole;
3-[5-(3-chloro-phenyl)-pyridin-3-yl]-1-(3-piperidin-1-yl-propyl)-indole;
dimethyl-{3-[3-(5-(3-chloro-phenyl)-pyridin-3-yl)-indol-1-yl]-propyl}-amine;
3-[5-(3-chloro-phenyl)-pyridin-3-yl]-1-(1-methyl-piperidin-3-ylmethyl)-indole;
3-[5-(3-chloro-phenyl)-pyridin-3-yl]-1-[3-(4-methyl-piperazin-1-yl)-propyl]-indole;
dimethyl-{2-[3-(5-(3-chloro-phenyl)-1-pyridin-3-yl)-indol-1-yl]-propyl}-amine;
dimethyl-{2-methyl-3-[3-(5-(3-chloro-phenyl)-pyridin-3-yl)-indol-1-yl]-propyl}-amine;
1-{2-[3-(5-(3-chloro-phenyl)-pyridin-3-yl)-indol-1-yl]-ethyl}-piperidine-4-carbonitrile;
3-[5-(3-chloro-phenyl)-pyridin-3-yl]-5-methoxy-indole;
3-[5-(3-chloro-phenyl)-pyridin-3-yl]-5-methoxy-1-(2-morpholin-4-yl-ethyl)-indole;
3-[5-(3-chloro-phenyl)-pyridin-3-yl]-5-methoxy-1-(2-piperidin-1-yl-ethyl)-indole;
3-[5-(3-chloro-phenyl)-pyridin-3-yl]-5-methoxy-1-(3-piperidin-1-yl-propyl)-indole;
dimethyl-{3-[3-(5-(3-chloro-phenyl)-pyridin-3-yl)-5-methoxy-indol-1-yl]-propyl}-amine;
3-[5-(3-chloro-phenyl)-pyridin-3-yl]-1-(1-methyl-piperidin-3-ylmethyl)-5-methoxy-indole;
3-[5-(3-chloro-phenyl)-pyridin-3-yl]-1-[3-(4-methyl-piperazin-1-yl)-propyl]-5-methoxy-indole;
dimethyl-{2-[3-(5-(3-chloro-phenyl)-1-pyridin-3-yl)-5-methoxy-indol-1-yl]-propyl}-amine;
dimethyl-{2-methyl-3-[3-(5-(3-chloro-phenyl)-pyridin-3-yl)-5-methoxy-indol-1-yl]-propyl}-amine;
1-{2-[3-(5-(3-chloro-phenyl)-pyridin-3-yl)-5-methoxy-indol-1-yl]-ethyl}-piperidine-4-carbonitrile;
4-chloro-3-[5-(3-chloro-phenyl)-pyridin-3-yl]-indole;
4-chloro-3-[5-(3-chloro-phenyl)-pyridin-3-yl]-1-(2-morpholin-4-yl-ethyl)-indole;
4-chloro-3-[5-(3-chloro-phenyl)-pyridin-3-yl]-1-(2-piperidin-1-yl-ethyl)-indole;
4-chloro-3-[5-(3-chloro-phenyl)-pyridin-3-yl]-1-(3-piperidin-1-yl-propyl)-indole;
dimethyl-{3-[4-chloro-3-(5-(3-chloro-phenyl)-pyridin-3-yl)-indol-1-yl]-propyl}-amine;
4-chloro-3-[5-(3-chloro-phenyl)-pyridin-3-yl]-1-(1-methyl-piperidin-3-ylmethyl)-indole;
4-chloro-3-[5-(3-chloro-phenyl)-pyridin-3-yl]-1-[3-(4-methyl-piperazin-1yl)-propyl]-indole;
dimethyl-{2-[4-chloro-3-(5-(3-chloro-phenyl)-1-pyridin-3-yl)-indol-1-yl]-propyl}-amine;
dimethyl-{2-methyl-3-[4-chloro-3-(5-(3-chloro-phenyl)-pyridin-3-yl)-indol-1-yl]-propyl}-amine;
1-{2-[4-chloro-3-(5-(3-chloro-phenyl)-pyridin-3-yl)-indol-1-yl]-ethyl}-piperidine-4-carbonitrile;
5-chloro-3-[5-(3-chloro-phenyl)-pyridin-3-yl]-indole;
5-chloro-3-[5-(3-chloro-phenyl)-pyridin-3-yl]-1-(2-morpholin-4-yl-ethyl)-indole;

5-chloro-3-[5-(3-chloro-phenyl)-pyridin-3-yl]-1-(2-piperidin-1-yl-ethyl)-indole;
5-chloro-3-[5-(3-chloro-phenyl)-pyridin-3-yl]-1-(3-piperidin-1-yl-propyl)-indole;
dimethyl-{3-[5-chloro-3-(5-(3-chloro-phenyl)-pyridin-3-yl)-indol-1-yl]-propyl}-amine;
5-chloro-3-[5-(3-chloro-phenyl)-pyridin-3-yl]-1-(1-methyl-piperidin-3-ylmethyl)-indole;
5-chloro-3-[5-(3-chloro-phenyl)-pyridin-3-yl]-1-[3-(4-methyl-piperazin-1-yl)-propyl)-indole;
dimethyl-{2-[5-chloro-3-(5-(3-chloro-phenyl)-1-pyridin-3-yl)-indol-1-yl]-propyl}-amine;
dimethyl-{2-methyl-3-[5-chloro-3-(5-(3-chloro-phenyl)-pyridin-3-yl)-indol-1-yl]-propyl}-amine;
1-{2-[5-chloro-3-(5-(3-chloro-phenyl)-pyridin-3-yl)-indol-1-yl]-ethyl}-piperidine-4-carbonitrile;
3-[5-(3-chloro-phenyl)-pyridin-3-yl]-7-methoxy-indole;
3-[5-(3-chloro-phenyl)-pyridin-3-yl]-7-methoxy-1-(2-morpholin-4-yl-ethyl)-indole;
3-[5-(3-chloro-phenyl)-pyridin-3-yl]-1 –7-methoxy-1-(2-piperidin-1-yl-ethyl)-indole;
3-[5-(3-chloro-phenyl)-pyridin-3-yl]-7-methoxy-1-(3-piperidin-1-yl-propyl)-indole;
dimethyl-{3-[3-(5-(3-chloro-phenyl)-pyridin-3-yl)-7-methoxy-indol-1-yl]-propyl}-amine;
3-[5-(3-chloro-phenyl)-pyridin-3-yl]-1-(1-methyl-piperidin-3-ylmethyl)-7-methoxy-indole;
3-[5-(3-chloro-phenyl)-pyridin-3-yl]-1-[3-(4-methyl-piperazin-1-yl)-propyl)-7-methoxy-indole;
dimethyl-{2-[3-(5-(3-chloro-phenyl)-1-pyridin-3-yl)-7-methoxy-indol-1-yl]-propyl}-amine;
dimethyl-{2-methyl-3-[3-(5-(3-chloro-phenyl)-pyridin-3-yl)-7-methoxy-indol-1-yl]-propyl}-amine;
1-{2-[3-(5-(3-chloro-phenyl)-pyridin-3-yl)-7-methoxy-indol-1-yl]-ethyl}-piperidine-4-carbonitrile;
6-chloro-3-[5-(3-chloro-phenyl)-pyridin-3-yl]-indole;
6-chloro-3-[5-(3-chloro-phenyl)-pyridin-3-yl]-1-(2-morpholin-4-yl-ethyl)-indole;
6-chloro-3-[5-(3-chloro-phenyl)-pyridin-3-yl]-1-(2-piperidin-1-yl-ethyl)-indole;
6-chloro-3-[5-(3-chloro-phenyl)-pyridin-3-yl]-1-(3-piperidin-1-yl-propyl)-indole;
dimethyl-{3-[6-chloro-3-(5-(3-chloro-phenyl)-pyridin-3-yl)-indol-1-yl]-propyl}-amine;
6-chloro-3-[5-(3-chloro-phenyl)-pyridin-3-yl]-1-(1-methyl-piperidin-3-ylmethyl)-indole;
6-chloro-3-[5-(3-chloro-phenyl)-pyridin-3-yl]-1-[3-(4-methyl-piperazin-1-yl)-propyl)-indole;
dimethyl-{2-[6-chloro-3-(5-(3-chloro-phenyl)-1-pyridin-3-yl)-indol-1-yl]-propyl}-amine;
dimethyl-{2-methyl-3-[6-chloro-3-(5-(3-chloro-phenyl)-pyridin-3-yl)-indol-1-yl]-propyl}-amine;
1-{2-[6-chloro-3-(5-(3-chloro-phenyl)-pyridin-3-yl)-indol-1-yl]-ethyl}-piperidine-4-carbonitrile;
3-[5-(3-chloro-phenyl)-pyridin-3-yl]-indole-5-carbonitrile;
3-[5-(3-chloro-phenyl)-pyridin-3-yl]-1-(2-morpholin-4-yl-ethyl)-indole-5-carbonitrile;
3-[5-(3-chloro-phenyl)-pyridin-3-yl]-1-(2-piperidin-1-yl-ethyl)-indole-5-carbonitrile;
3-[5-(3-chloro-phenyl)-pyridin-3-yl]-1-(3-piperidin-1-yl-propyl)-indole-5-carbonitrile;
1-(3-dimethylamino-propyl)-3-[5-(3-chloro-phenyl)-pyridin-3-yl]-indole-5-carbonitrile;
3-[5-(3-chloro-phenyl)-pyridin-3-yl]-1-(1-methyl-piperidin-3-ylmethyl)-indole-5-carbonitrile;
3-[5-(3-chloro-phenyl)-pyridin-3-yl]-1-[3-(4-methyl-piperazin-1-yl)-propyl)-indole-5-carbonitrile;
1-(2-dimethylamino-propyl)-3-[5-(3-chloro-phenyl)-pyridin-3-yl]-indole-5-carbonitrile;
1-(1-dimethylamino-2-methyl-propyl)-3-[5-(3-chloro-phenyl)-pyridin-3-yl]-indole-5-carbonitrile;
1-[2-(4-cyano-piperidin-1-yl-ethyl]-3-[5-(3-chloro-phenyl)-pyridin-3-yl]-indole-5-carbonitrile;
3-[5-(3-chloro-phenyl)-pyridin-3-yl]-indole-4-carboxylic acid methyl ester;
3-[5-(3-chloro-phenyl)-pyridin-3-yl]-1-(2-morpholin-4-yl-ethyl)-indole-4-carboxylic acid methyl ester;
3-[5-(3-chloro-phenyl)-pyridin-3-yl]-1-(2-piperidin-1-yl-ethyl)-indole-4-carboxylic acid methyl ester;
3-[5-(3-chloro-phenyl)-pyridin-3-yl]-1-(3-piperidin-1-yl-propyl)-indole-4-carboxylic acid methyl ester;
1-(3-dimethylamino-propyl)-3-[5-(3-chloro-phenyl)-pyridin-3-yl]-indole-4-carboxylic acid methyl ester;
3-[5-(3-chloro-phenyl)-pyridin-3-yl]-1-(1-methyl-piperidin-3-ylmethyl)-indole-4-carboxylic acid methyl ester;
3-[5-(3-chloro-phenyl)-pyridin-3-yl]-1-[3-(4-methyl-piperazin-1-yl)-propyl)-indole-4-carboxylic acid methyl ester;
1-(2-dimethylamino-propyl)-3-[5-(3-chloro-phenyl)-pyridin-3-yl]-indole-4-carboxylic acid methyl ester;
1-(1-dimethylamino-2-methyl-propyl)-3-[5-(3-chloro-phenyl)-pyridin-3-yl]-indole-4-carboxylic acid methyl ester;
1-[2-(4-cyano-piperidin-1-yl-ethyl-3-[5-(3-chloro-phenyl)-pyridin-3-yl]-indole-4-carboxylic acid methyl ester;
3-[5-(3-chloro-phenyl)-pyridin-3-yl]-pyrrolo[2 ,31 pyridine;
3-[5-(3-chloro-phenyl)-pyridin-3-yl]-1-(2-morpholin-4-yl-ethyl)-pyrrolo[2,3]pyridine;
3-[5-(3-chloro-phenyl)-pyridin-3-yl]-1-(2-piperidin-1-yl-ethyl)-pyrrolo[2,3]pyridine;
3-[5-(3-chloro-phenyl)-pyridin-3-yl]-1-(3-piperidin-1-yl-propyl)-pyrrolo[2,3]pyridine;
dimethyl-{3-[3-(5-(3-chloro-phenyl)-pyridin-3-yl)-pyrrolo[2,3]pyridin-1-yl]-propyl}-amine;
3-[5-(3-chloro-phenyl)-pyridin-3-yl]-1-(1-methyl-piperidin-3-ylmethyl)-pyrrolo[2,3]pyridine;
3-[5-(3-chloro-phenyl)-pyridin-3-yl]-1-[3-(4-methyl-piperazin-1-yl)-propyl)-pyrrolo[2,3]pyridine;
dimethyl-{2-[3-(5-(3-chloro-phenyl)-1-pyridin-3-yl)-pyrrolo[2,3]pyridin-1-yl]-propyl}-amine;
dimethyl-{2-methyl-3-[3-(5-(3-chloro-phenyl)-pyridin-3-yl)-pyrrolo[2,3]pyridin-1-yl]-propyl}-amine;
1-{2-[3-(5-(3-chloro-phenyl)-pyridin-3-yl)-pyrrolo[2,3]pyridin-1-yl]-ethyl}piperidine-4-carbonitrile;
3-[5-(4-chloro-phenyl)-pyridin-3-yl]-indole;
3-[5-(4-chloro-phenyl)-pyridin-3-yl]-1-(2-morpholin-4-yl-ethyl)-indole;
3-[5-(4-chloro-phenyl)-pyridin-3-yl]-1-(2-piperidin-1-yl-ethyl)-indole;
3-[5-(4-chloro-phenyl)-pyridin-3-yl]-1-(3-piperidin-1-yl-propyl)-indole;

dimethyl-{3-[3-(5-(4-chloro-phenyl)-pyridin-3-yl)-indol-1-yl]-propyl}-amine;
3-[5-(4-chloro-phenyl)-pyridin-3-yl]-1-(l1-methyl-piperidin-3-ylmethyl)-indole;
3-[5-(4-chloro-phenyl)-pyridin-3-yl]-1-[3-(4-methyl-piperazin-1-yl)-propyl)-indole;
dimethyl-{2-[3-(5-(4-chloro-phenyl)-1-pyridin-3-yl)-indol-1-yl]-propyl}-amine;
dimethyl-{2-methyl-3-[3-(5-(4-chloro-phenyl)-pyridin-3-yl)-indol-1-yl]-propyl}-amine;
1-{2-[3-(5-(4-chloro-phenyl)-pyridin-3-yl)-indol-1-yl]-ethyl}-piperidine-4-carbonitrile;
3-[5-(4-chloro-phenyl)-pyridin-3-yl]-5-methoxy-indole;
3-[5-(4-chloro-phenyl)-pyridin-3-yl]-5-methoxy-1-(2-morpholin-4-yl-ethyl)-indole;
3-[5-(4-chloro-phenyl)-pyridin-3-yl]-5-methoxy-1-(2-piperidin-1-yl-ethyl)-indole;
3-[5-(4-chloro-phenyl)-pyridin-3-yl]-5-methoxy-1-(3-piperidin-1-yl-propyl)-indole;
dimethyl-{3-[3-(5-(4-chloro-phenyl)-pyridin-3-yl)-5-methoxy-indol-1-yl]-propyl}-amine;
3-[5-(4-chloro-phenyl)-pyridin-3-yl]-1-(1-methyl-piperidin-3-ylmethyl)-5-methoxy-indole;
3-[5-(4-chloro-phenyl)-pyridin-3-yl]-1-[3-(4-methyl-piperazin-1-yl)-propyl)-5-methoxy-indole;
dimethyl-{2-[3-(5-(4-chloro-phenyl)-1-pyridin-3-yl)-5-methoxy-indol-1-yl]-propyl}-amine;
dimethyl-{2-methyl-3-[3-(5-(4-chloro-phenyl)-pyridin-3-yl)-5-methoxy-indol-1-yl]-propyl}-amine;
1-{2-[3-(5-(4-chloro-phenyl)-pyridin-3-yl)-5-methoxy-indol-1-yl]-ethyl}-piperidine-4-carbonitrile;
4-chloro-3-[5-(4-chloro-phenyl)-pyridin-3-yl]-indole;
4-chloro-3-[5-(4-chloro-phenyl)-pyridin-3-yl]-1-(2-morpholin-4-yl-ethyl)-indole;
4-chloro-3-[5-(4-chloro-phenyl)-pyridin-3-yl]-1-(2-piperidin-1-yl-ethyl)-indole;
4-chloro-3-[5-(4-chloro-phenyl)-pyridin-3-yl]-1-(3-piperidin-1-yl-propyl)-indole;
dimethyl-{3-[4-chloro-3-(5-(4-chloro-phenyl)-pyridin-3-yl)-indol-1-yl]-propyl}-amine;
4-chloro-3-[5-(4-chloro-phenyl)-pyridin-3-yl]-1-(1-methyl-piperidin-3-ylmethyl)-indole;
4-chloro-3-[5-(4-chloro-phenyl)-pyridin-3-yl]-1-[3-(4-methyl-piperazin-1-yl)-propyl)-indole;
dimethyl-{2-[4-chloro-3-(5-(4-chloro-phenyl)-1-pyridin-3-yl)-indol-1-yl]-propyl}-amine;
dimethyl-{2-methyl-3-[4-chloro-3-(5-(4-chloro-phenyl)-pyridin-3-yl)-indol-1-yl]-propyl}-amine;
1-{2-[4-chloro-3-(5-(4-chloro-phenyl)-pyridin-3-yl)-indol-1-yl]-ethyl}-piperidine-4-carbonitrile;
5-chloro-3-[5-(4-chloro-phenyl)-pyridin-3-yl]-indole;
5-chloro-3-[5-(4-chloro-phenyl)-pyridin-3-yl]-1-(2-morpholin-4-yl-ethyl)-indole;
5-chloro-3-[5-(4-chloro-phenyl)-pyridin-3-yl]-1-(2-piperidin-1-yl-ethyl)-indole;
5-chloro-3-[5-(4-chloro-phenyl)-pyridin-3-yl]-1-(3-piperidin-1-yl-propyl)-indole;
dimethyl-{3-[5-chloro-3-(5-(4-chloro-phenyl)-pyridin-3-yl)-indol-1-yl]-propyl}-amine;
5-chloro-3-[5-(4-chloro-phenyl)-pyridin-3-yl]-1-(1-methyl-piperidin-3-ylmethyl)-indole;
5-chloro-3-[5-(4-chloro-phenyl)-pyridin-3-yl]-1-[3-(4-methyl-piperazin-1-yl)-propyl)-indole;
dimethyl-{2-[5-chloro-3-(5-(4-chloro-phenyl)-1-pyridin-3-yl)-indol-1-yl]-propyl)-amine;
dimethyl-{2-methyl-3–15-chloro-3-(5-(4-chloro-phenyl)-pyridin-3-yl)-indol-1-yl]-propyl}-amine;
1-{2-[5-chloro-3-(5-(4-chloro-phenyl)-pyridin-3-yl)-indol-1-yl]-ethyl}-piperidine-4-carbonitrile;
3-[5-(4-chloro-phenyl)-pyridin-3-yl]-7-methoxy-indole;
3-[5-(4-chloro-phenyl)-pyridin-3-yl]-7-methoxy-1-(2-morpholin-4-yl-ethyl)-indole;
3-[5-(4-chloro-phenyl)-pyridin-3-yl]-7-methoxy-1-(2-piperidin-1-yl-ethyl)-indole;
3-[5-(4-chloro-phenyl)-pyridin-3-yl]-7-methoxy-1-(3-piperidin-1-yl-propyl)-indole;
dimethyl-{3-[3-(5-(4-chloro-phenyl)-pyridin-3-yl-7-methoxy-indol-1-yl]-propyl}-amine;
3-[5-(4-chloro-phenyl)-pyridin-3-yl]-1-(1-methyl-piperidin-3-ylmethyl)-7-methoxy-indole;
3-[5-(4-chloro-phenyl)-pyridin-3-yl]-1-[3-(4-methyl-piperazin-1-yl)-propyl)-7-methoxy-indole;
dimethyl-{2-[3-(5-(3-chloro-phenyl)-1-pyridin-3-yl)-7-methoxy-indol-1-yl]-propyl}-amine;
dimethyl-{2-methyl-3-[3-(5-(4-chloro-phenyl)-pyridin-3-yl)-7-methoxy-indol-1-yl]-propyl}-amine;
1-{2-[3-(5-(4-chloro-phenyl)-pyridin-3-yl)-7-methoxy-indol-1-yl]-ethyl}-piperidine-4-carbonitrile;
6-chloro-3-[5-(4-chloro-phenyl)-pyridin-3-yl]-indole;
6-chloro-3-[5-(4-chloro-phenyl)-pyridin-3-yl]-1-(2-morpholin-4-yl-ethyl)-indole;
6-chloro-3-[5-(4-chloro-phenyl)-pyridin-3-yl]-1-(2-piperidin-1-yl-ethyl)-indole;
6-chloro-3-[5-(4-chloro-phenyl)-pyridin-3-yl]-1-(3-piperidin-1-yl-propyl)-indole;
dimethyl-{3-[6-chloro-3-(5-(4-chloro-phenyl)-pyridin-3-yl)-indol-1-yl]-propyl}-amine;
6-chloro-3-[5-(4-chloro-phenyl)-pyridin-3-yl]-1-(1-methyl-piperidin-3-ylmethyl)-indole;
6-chloro-3-[5-(4-chloro-phenyl)-pyridin-3-yl]-1-[3-(4-methyl-piperazin-1yl)-propyl)-indole;
dimethyl-{2-[6-chloro-3-(5-(4-chloro-phenyl)-1-pyridin-3-yl)-indol-1-yl]-propyl}-amine;
dimethyl-(2-methyl-3-[6-chloro-3-(5-(4-chloro-phenyl)-pyridin-3-yl)-indol-1-yl]-propyl}-amine;
1-{2-[6-chloro-3-(5-(4-chloro-phenyl)-pyridin-3-yl)-indol-1-yl]-ethyl}-piperidine-4-carbonitrile;
3-[5-(4-chloro-phenyl)-pyridin-3-yl]-indole-5-carbonitrile;
3-[5-(4-chloro-phenyl)-pyridin-3-yl]-1-(2-morpholin-4-yl-ethyl)-indole-5-carbonitrile;
3-[5-(4-chloro-phenyl)-pyridin-3-yl]-1-(2-piperidin-1-yl-ethyl)-indole-5-carbonitrile;
3-[5-(4-chloro-phenyl)-pyridin-3-yl]-1-(3-piperidin-1-yl-propyl)-indole-5-carbonitrile;
1-(3-dimethylamino-propyl)-3-[5-(4-chloro-phenyl)-pyridin-3-yl]-indole-5-carbonitrile;

3-[5-(4-chloro-phenyl)-pyridin-3-yl]-1-(1-methyl-piperidin-3-ylmethyl)-indole-5-carbonitrile;
3-[5-(4-chloro-phenyl)-pyridin-3-yl]-1-[3-(4-methyl-piperazin-1-yl)-propyl)-indole-5-carbonitrile;
1-(2-dimethylamino-propyl)-3-[5-(4-chloro-phenyl)-pyridin-3-yl]-indole-5-carbonitrile;
1-(1-dimethylamino-2-methyl-propyl)-3-[5-(4-chloro-phenyl)-pyridin-3-yl]-indole-5-carbonitrile;
1-[2-(4-cyano-piperidin-1-yl-ethyl]-3-[5-(4-chloro-phenyl)-pyridin-3-yl]-indole-5-carbonitrile;
3-[5-(4-chloro-phenyl)-pyridin-3-yl]-indole-4-carboxylic acid methyl ester;
3-[5-(4-chloro-phenyl)-pyridin-3-yl]-1-(2-morpholin-4-yl-ethyl)-indole-4-carboxylic acid methyl ester;
3-[5-(4-chloro-phenyl)-pyridin-3-yl]-1-(2-piperidin-1-yl-ethyl)-indole-4-carboxylic acid methyl ester;
3-[5-(4-chloro-phenyl)-pyridin-3-yl]-11-(3-piperidin-1-yl-propyl)-indole-4-carboxylic acid methyl ester;
1-(3-dimethylamino-propyl)-3-[5-(4-chloro-phenyl)-pyridin-3-yl]-indole-4-carboxylic acid methyl ester;
3-[5-(4-chloro-phenyl)-pyridin-3-yl]-1-(1-methyl-piperidin-3-ylmethyl)-indole-4-carboxylic acid methyl ester;
3-[5-(4-chloro-phenyl)-pyridin-3-yl]-1-[3-(4-methyl-piperazin-1-yl)-propyl)-indole-4-carboxylic acid methyl ester;
1-(2-dimethylamino-propyl)-3-[5-(4-chloro-phenyl)-pyridin-3-yl]-indole-4-carboxylic acid methyl ester;
1-(1-dimethylamino-2-methyl-propyl)-3-[5-(4-chloro-phenyl)-pyridin-3-yl]-indole-4-carboxylic acid methyl ester;
1-[2-(4-cyano-piperidin-1-yl-ethyl]-3-[5-(4-chloro-phenyl)-pyridin-3-yl]-indole-4-carboxylic acid methyl ester;
3-[5-(4-chloro-phenyl)-pyridin-3-yl]-pyrrolo[2,3]pyridine;
3-[5-(4-chloro-phenyl)-pyridin-3-yl]-1-(2-morpholin-4-yl-ethyl)-pyrrolo[2,3]pyridine;
3-[5-(4-chloro-phenyl)-pyridin-3-yl]-1-(2-piperidin-1-yl-ethyl)-pyrrolo[2,3]pyridine;
3-[5-(4-chloro-phenyl)-pyridin-3-yl]-1-(3-piperidin-1-yl-propyl)-pyrrolo[2,3]pyridine; dimethyl-{3-[3-(5-(4-chloro-phenyl)-pyridin-3-yl)-pyrrolo[2,3]pyridin-1-yl]-propyl}-amine;
3-[5-(4-chloro-phenyl)-pyridin-3-yl]-1-(1-methyl-piperidin-3-ylmethyl)-pyrrolo[2,3]pyridine;
3-[5-(4-chloro-phenyl)-pyridin-3-yl]-1-[3-(4-methyl-piperazin-1-yl)-propyl)-pyrrolo[2,3]pyridine
dimethyl-{2-[3-(5-(4-chloro-phenyl)-1-pyridin-3-yl)-pyrrolo[2,3]pyridin-1-yl]-propyl}-amine;
dimethyl-{2-methyl-3-[3-(5-(4-chloro-phenyl)-pyridin-3-yl)-pyrrolo[2,3]pyridin-1-yl]-propyl}-amine; and
1-{2-[3-(5-(4-chloro-phenyl)-pyridin-3-yl)-pyrrolo[2,3]pyridin-1-yl]-ethyl}piperidine-4-carbonitrile.

A more preferred embodiment is a compound selected from a group consisting of:

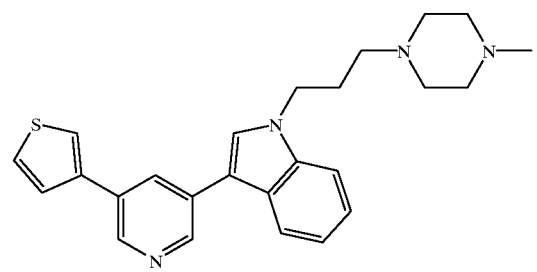

1-[3-(4-methyl-piperazin-1-yl)-propyl]-3-(5-thiophen-3-yl-pyridin-3-yl)-1H-indole;

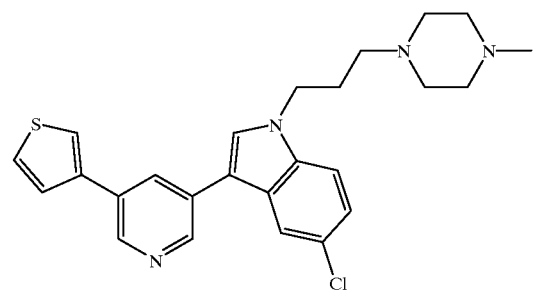

5-chloro-1-[3-(4-methyl-piperazin-1-yl)-propyl]-3-(5-thiophen-3-yl-pyridin-3-yl)-1H-indole;

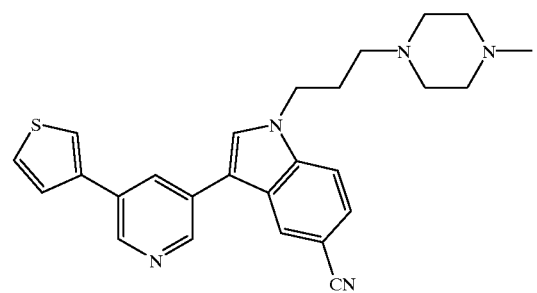

1-[3-(4-methyl-piperazin-1-yl)-propyl]-3-(5-thiophen-3-yl-yl-pyridin-3-yl)-1-H-indole-5-carbonitrile;

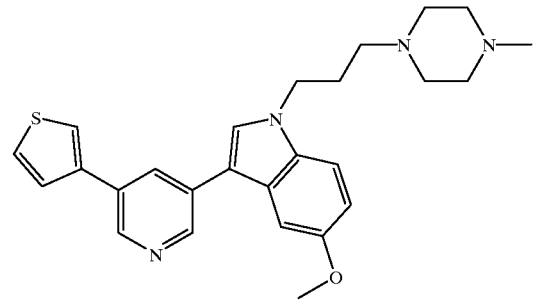

5-methoxy-1-[3-(4-methyl-piperazin-1-yl)-propyl]-3-(5-thiophen-3-yl-pyridin-3-yl)-1H-indole;

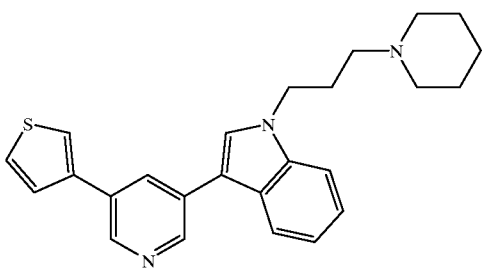

1-(3-piperidin-1-yl-propyl-3-(5-thiophen-3-yl-pyridin-3-yl)-1H-indole; and

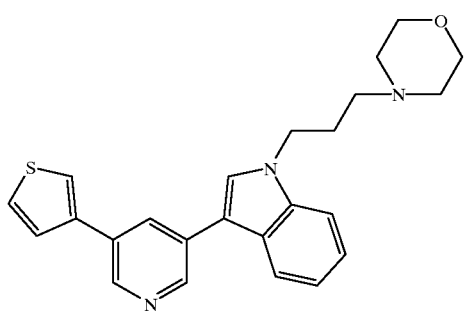

1-(2-morpholin-4-yl-ethyl)-3-(5-thiophen-3-yl-pyridin-3-yl)-1H-indole.

Also included is a method of treating or preventing a tyrosine kinase dependent disease or condition in a mammal which comprises administering to a mammalian patient in need of such treatment a therapeutically effective amount of a compound of formula I or a pharmaceutically acceptable salt or hydrate thereof.

Also included is a method of treating or preventing cancer in a mammalian patient in need of such treatment which is comprised of admininstering to said patient a therapeutically effective amount of a compound of formula I or a pharmaceutically acceptable salt or hydrate thereof.

Also included in the present invention is a method of treating or preventing diseases in which neoangiogenesis is implicated, which is comprised of administering to a mammalian patient in need of such treatment a compound of formula I or a pharmaceutically acceptable salt or hydrate thereof in a therapeutically effective amount.

More particularly, a method of treating or preventing ocular disease in which neoangiogenesis occurs is included herein, which is comprised of administering to a mammalian patient in need of such treatment a compound of formula I or a pharmaceutically acceptable salt or hydrate thereof in a therapeutically effective amount.

More particularly, a method of treating or preventing retinal vascularization is included herein, which is comprised of administering to a mammalian patient in need of such treatment a compound of formula I or a pharmaceutically acceptable salt or hydrate thereof in a therapeutically effective amount. Diabetic retinopathy is an example of a disease in which neoangiogenesis or retinal vascularization is part of the overall disease etiology. Also included is a method of treating or preventing age-related macular degeneration. The methods of treatment are a more preferred embodiment of the present invention.

These and other aspects of the invention will be apparent from the teachings contained herein.

The compounds of the present invention may have asymmetric centers and occur as racemates, racemic mixtures, and as individual diastereomers, with all possible isomers, including optical isomers, being included in the present invention. When any variable (e.g. aryl, heterocycle, $R^1$, $R^2$ etc.) occurs more than one time in any constituent, its definition on each occurrence is independent of every other occurrence. Also, combinations of substituents and/or variables are permissible only if such combinations result in stable compounds. For example, "$NR^c_2$" may be any of the following if $R^c$ is defined as H, $CH_3$, or OH: $N(OH)(CH_3)$, $NH_2$, $N(CH_3)_2$, $NH(CH_3)$, etc.

As used herein, "alkyl" is intended to include both branched and straight-chain saturated, monovalent aliphatic hydrocarbon groups having the specified number of carbon atoms. For example, $C_{1-10}$, as in ($C_{1-10}$)alkyl is defined to identify the group as having 1, 2, 3, 4, 5, 6, 7, 8, 9 or 10 carbons in a linear or branched arrangement, such that ($C_{1-10}$) alkyl specifically includes methyl, ethyl, propyl, butyl, pentyl, hexyl, heptyl, octyl, nonyl and decyl. "Alkoxy" represents an alkyl group of indicated number of carbon atoms attached through an oxygen bridge. "Halogen" or "halo" as used herein means fluoro, chloro, bromo and iodo. Cycloalkyl refers to a cyclic or bicyclic saturated chain of three to ten carbons. Examples of cycloalkyls are cyclopropyl, cyclobutyl, cyclopentyl, cyclohexyl, tetrahydro-naphthalene, etc.

The term "alkylenyl" or "alkylene" refers to a divalent alkane (hydrocarbon) derived radical containing from 1 to 10 carbon atoms unless otherwise defined. It may be straight, branched or cyclic. Examples of alkylenes are —$CH_2$—, —$CH_2CH_2$—, —$CH(CH_3)CH_2$—, etc. Similarly, "—$C_{1-6}$ alkylene-O—$C_{1-6}$ alkyl" includes the following: —$CH_2CH_2$—O—$CH_2CH_3$, —$CH(CH_3)CH_2$—O—$CH_2CH_3$, etc.

As used herein, "aryl" is intended to mean any stable monocyclic or bicyclic carbon ring of up to 7 members in each ring, wherein at least one ring is aromatic and attachment to the substituted group is via the aromatic ring. Examples of such aryl elements include phenyl, naphthyl, tetrahydronaphthyl, indanyl, biphenyl, phenanthryl, anthryl or acenaphthyl. An aryl group may be substituted with one to three substituents selected from $R^a$.

The term heteroaryl, as used herein, represents, a 5- to 7-membered aromatic heterocycle containing from 1 to 4 heteroatoms selected from the group consisting of O, N and S, and includes any bicyclic group in which any of the above-defined heteroaryl rings is fused to a benzene ring. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, pyrazinyl, pyridazinyl, pyridinyl, pyrimidinyl, and pyrrolyl. A heteroaryl group may be substituted with one to three substituents selected from $R^a$.

As appreciated by those skilled in the art, "halo " or "halogen" as used herein is intended to include chloro, fluoro, bromo and iodo. The term "heterocycle" or "heterocyclyl" as used herein is intended to mean a 5- to 10-membered aromatic or nonaromatic heterocycle containing from 1 to 4 heteroatoms selected from the group consisting of O, N and S, and includes bicyclic groups. The term "heterocyclyl", therefore, is intended to encompass the definition of "heteroaryl" described above. Examples of heterocyclyl include, but are not limited to, the following: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. The heterocyclyl group may be substituted with one to three substituents selected from $R^a$.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If used, the phrase "optionally substituted with one or more substituents" means that the group to which the phrase refers is either unsubstituted (i.e., only hydrogen atoms present at any substitutable position) or substituted with one or more substituents, where there can be as many substituents from the selected list as are possible and still form a stable compound. Preferentially, the group is unsubstituted or substituted with one to three substituents from the list.

Preferrentially, only one of X, Y and Z is N, and the remainder are C—H. Most preferrentially Y is N and X and Z are C—H.

Preferrentially, $R^1$ is heterocyclyl. More preferrentially $R^1$ is heteroaryl. And most preferrentailly $R^1$ is thiophene.

Preferrentially, W is C—H. Preferrentially, $R^2$ is alkyl substituted with one or two groups selected from $R^a$. The more preferred definition of $R^a$ is $NR^7R^8$, where $R^7$ and $R^8$ are alklyl, alkylene-O-alkyl, or $NR^7R^8$ is taken together to form a heterocyclyl, optionally substituted with CN, halo or alkyl. Preferred heterocyclyls in this context are piperidine, piperazine, and azepin. Preferrentially $R^3$ is H, CN, $CO_2R$, OR, halo or alkyl.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the compounds of this invention can be synthesized from the compounds of this invention which contain a basic moiety by conventional chemical methods. Generally, the salts are prepared either by ion exchange chromatography or by reacting the free base with stoichiometric amounts or with an excess of the desired salt-forming inorganic or organic acid in a suitable solvent or various combinations of solvents.

As used herein, the term "composition" is intended to encompass a product comprising the specified ingredients in the specified amounts, as well as any products which result, either directly or indirectly, from combination of the specified ingredients in the specified amounts.

The compounds of this invention may be prepared by employing reactions as shown in the schemes below, in addition to other standard manipulations as are known in the literature or exemplified in the experimental procedures. These schemes, therefore, are not limited by the compounds listed nor by any particular substituents employed for illustrative purposes. Substituent numbering as shown in the Schemes do not necessarily correlate to that used in the claims.

As shown in Scheme 1, the desired compounds can be prepared via the palladium catalyzed coupling of a boronic indole with a bromopyridine substrate. Analogs may also be prepared via the alternative route illustrated in Scheme 2.

Scheme 1

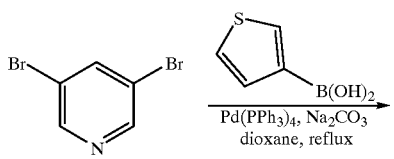

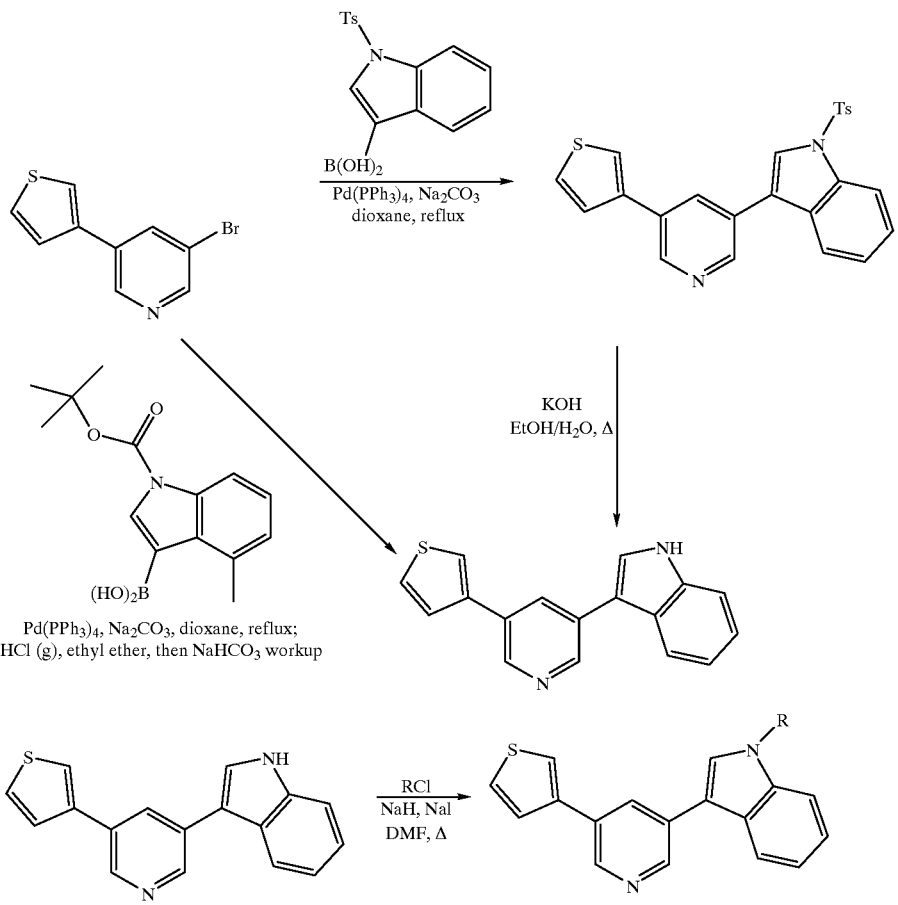
Scheme 2
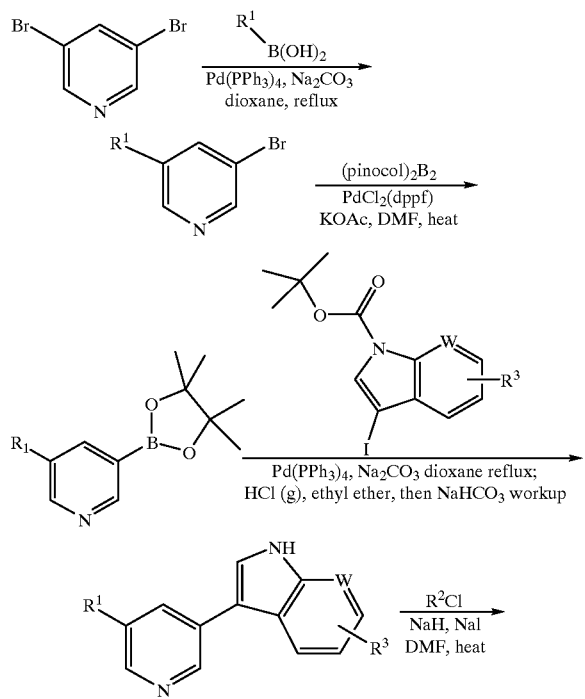

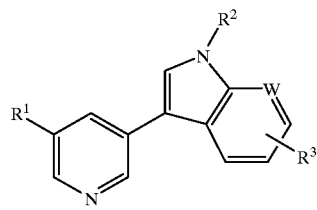

The invention described herein includes a pharmaceutical composition which is comprised of a compound of formula I or a pharmaceutically acceptable salt, hydrate or prodrug thereof in combination with a carrier. As used herein the terms "pharmaceutically acceptable salts" and "hydrates" refer to those salts and hydrated forms of the compound which would be apparent to the pharmaceutical chemist, i.e., those which favorably affect the physical or pharmacokinetic properties of the compound, such as solubility, palatability, absorption, distribution, metabolism and excretion. Other factors, more practical in nature, which are also important in the selection, are the cost of the raw materials, ease of crystallization, yield, stability, solubility, hygroscopicity and flowability of the resulting bulk drug.

When a compound of formula I is present as a salt or hydrate which is non-pharmaceutically acceptable, this can be converted to a salt or hydrate form which is pharmaceutically acceptable in accordance with the present invention.

When the compound is negatively charged, it is balanced by a counterion, e.g., an alkali metal cation such as sodium or potassium. Other suitable counterions include calcium, magnesium, zinc, ammonium, or alkylammonium cations such as tetramethylammonium, tetrabutylammonium, choline, triethylhydroammonium, meglumine, triethanolhydroammonium, etc. An appropriate number of counterions is associated with the molecule to maintain overall charge neutrality. Likewise when the compound is positively charged, e.g., protonated, an appropriate number of negatively charged counterions is present to maintain overall charge neutrality.

Pharmaceutically acceptable salts also include acid addition salts. Thus, the compound can be used in the form of salts derived from inorganic or organic acids or bases. Examples include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Other pharmaceutically acceptable salts include the sulfate salt ethanolate and sulfate salts.

The compounds of the present invention, may have asymmetric centers and occur as racemates, racemic mixtures and as individual diastereomers, or enantiomers with all isomeric forms being included in the present invention. When any variable (e.g., aryl, heteroaryl, $R^1$, etc.) occurs more than one time in any constituent or in Formula I, its definition on each occcurence is independent of its definition at every other occurrence, unless otherwise stated.

The compounds of the invention can be formulated in a pharmaceutical composition by combining the compound with a pharmaceutically acceptable carrier. Examples of such compositions and carriers are set forth below.

The compounds may be employed in powder or crystalline form, in solution or in suspension. They may be administered orally, parenterally (intravenously or intramuscularly), topically, transdermally or by inhalation.

Thus, the carrier employed may be, for example, either a solid or liquid. Examples of solid carriers include lactose, terra alba, sucrose, talc, gelatin, agar, pectin, acacia, magnesium stearate, stearic acid and the like. Examples of liquid carriers include syrup, peanut oil, olive oil, water and the like. Similarly, the carrier for oral use may include time delay material well known in the art, such as glyceryl monostearate or glyceryl distearate alone or with a wax.

Topical applications may be formulated in carriers such as hydrophobic or hydrophilic bases to form ointments, creams, lotions, in aqueous, oleaginous or alcoholic liquids to form paints or in dry diluents to form powders. Such topical formulations can be used to treat ocular diseases as well as inflammatory diseases such as rheumatoid arthritis, psoriasis, contact dermatitis, delayed hypersensitivity reactions and the like.

Examples of oral solid dosage forms include tablets, capsules, troches, lozenges and the like. The size of the dosage form will vary widely, but preferably will be from about 25 mg to about 500 mg. Examples of oral liquid dosage forms include solutions, suspensions, syrups, emulsions, soft gelatin capsules and the like. Examples of injectable dosage forms include sterile injectable liquids, e.g., solutions, emulsions and suspensions. Examples of injectable solids would include powders which are reconstituted, dissolved or suspended in a liquid prior to injection.

In injectable compositions, the carrier is typically comprised of sterile water, saline or another injectable liquid, e.g., peanut oil for intramuscular injections. Also, various buffering agents, preservatives and the like can be included.

For the methods of treatment disclosed herein, dosages can be varied depending upon the overall condition of the patient, the nature of the illness being treated and other factors. An example of a suitable oral dosage range is from about 0.1 to about 80 mg/kg per day, in single or divided doses. An example of a suitable parenteral dosage range is from about 0.1 to about 80 mg/kg per day, in single or divided dosages, administered by intravenous or intramuscular injection. An example of a topical dosage range is from about 0.1 mg to about 150 mg, applied externally from about one to four times a day. An example of an inhalation dosage range is from about 0.01 mg/kg to about 1 mg/kg per day.

The compounds may be administered in conventional dosages as a single agent or in combination with other therapeutically active compounds.

EXAMPLES

Examples provided are intended to assist in a further understanding of the invention. Particular materials employed, species and conditions are intended to be further illustrative of the invention and not limiting of the reasonable scope thereof.

Example 1

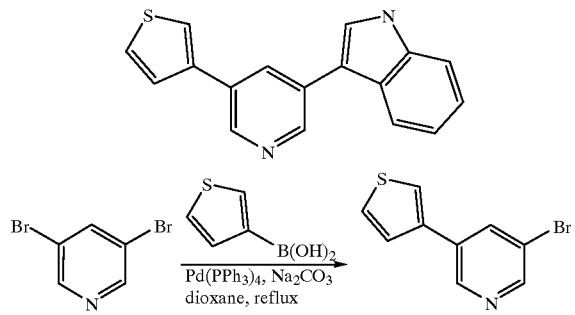

A deoxygenated solution of 3,5-dibromopyridine (4.00 g, 16.9 mmol, 1 equiv), 3-thiopheneboronic acid (2.38 g, 18.6 mmol, 1.10 equiv), Pd(PPh₃)₄ (781 mg, 0.676 mmol, 0.0433 equiv), and 2.0 M Na₂CO₃ (16.9 mL, 33.8 mmol, 2.00 equiv) in dioxane (40 ml) was heated under argon at reflux for 20 h. The reaction mixture was allowed to cool, then partitioned between water (200 mL) and ethyl acetate (2×300 mL). The combined organic layers were dried over sodium sulfate and concentrated. The residue was purified by flash column chromatography (5% ethyl acetate in dichloromethane) to afford 3-bromo-5-thiophen-3-yl-pyridine as a white solid.

¹H NMR (300 MHz, CDCl₃) d 8.78 (d, 1H, J=1.8 Hz), 8.59 (d, 1H, J=1.8 Hz), 8.02 (t, 1H, J=1.8 Hz), 7.56 (dd, 1H, J=2.8, 1.2 Hz), 7.47 (dd, 1H, J=4.8, 2.8 Hz), 7.37 (dd, 1H, J=4.8, 2.8 Hz); TLC (5% EtOAc in CH₂Cl₂), R_f=0.58.

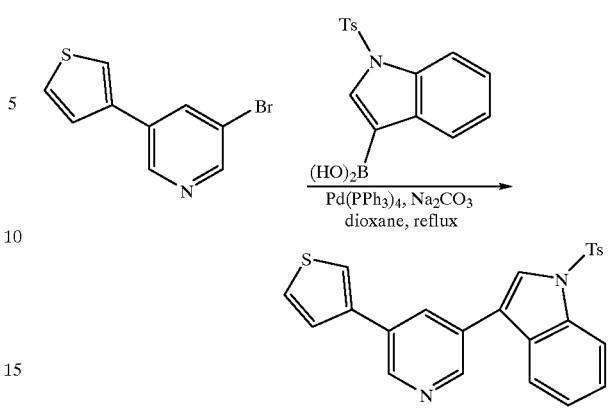

A deoxygenated solution of 3-bromo-5-thiophen-3-yl-pyridine (250 mg, 1.04 mmol, 1 equiv), 1-tosyl-3-indoleboronic acid (430 mg, 1.36 mmol, 1.31 equiv, prepared according to Zheng, Q; Yang, Y; Martin, A. R. Heterocycles 1994, 37, 1761), Pd(PPh₃)₄ (60 mg, 0.052 mmol, 0.050 equiv), and 2.0 M Na₂CO₃ (1.0 mL, 2.0 mmol, 1.9 equiv) in dioxane (10 ml) was heated under argon at reflux for 20 h. The reaction mixture was allowed to cool, then partitioned between water (100 mL) and ethyl acetate (2×100 mL). The combined organic layers were dried over sodium sulfate and concentrated. The residue was purified by flash column chromatography (40% ethyl acetate in hexane) to afford 3-(5-thiophen-3-yl-pyridin-3-yl)-1-(toluene-4-sulfonyl)-indole as a white foam.

¹H NMR (300 MHz, CDCl₃) d 8.86 (d, 1H, J=2.0 Hz), 8.77 (d, 1H, J=2.2 Hz), 8.09 (br d, 1H, J=8.1 Hz), 8.06 (t, 1H, J=2.2 Hz), 7.84 (d, 2H, J=8.5 Hz), 7.80 (s, 1H), 7.76 (br d, 1H, J=7.8 Hz), 7.59 (dd, 1H, J=2.7, 1.2 Hz), 7.48 (dd, 1H, J=5.1, 2.9 Hz), 7.44 (dd, 1H, J=5.1, 1.2 Hz), 7.41 (br t, J=7.3 Hz), 7.32 (br t, 1H, J=7.6 Hz), 7.26 (d, 2H, J=8.0 Hz), 2.36 (s, 3H); TLC (40% EtOAc in hexane), R_f=0.26.

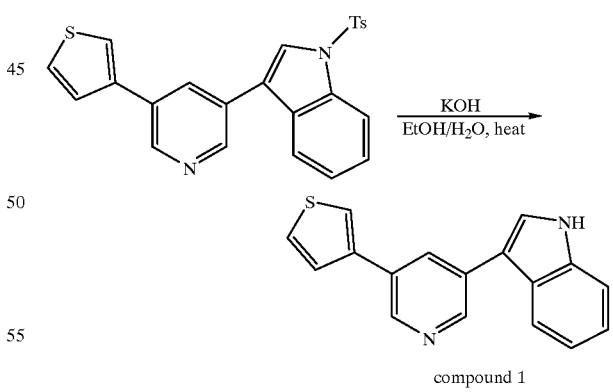

compound 1

A solution of 3-(5-thiophen-3-yl-pyridin-3-yl)-1-(toluene-4-sulfonyl)-indole (350 g, 0.812 mmol, 1 equiv) and KOH (228 mg, 4.06 mmol, 5.00 equiv) in a 2:1 mixture of ethanol and water (40 ml) was heated at reflux for 6 h. The reaction mixture was allowed to cool, then concentrated to dryness. The residual solid was suspended in water (200 mL) and extracted with ethyl acetate (2×100 mL). The combined organic layers were dried over Na₂SO₄ and concentrated. The solid residue was suspended in hot ethyl acetate (30 mL) and filtered to afford the titled compound as a white solid.

$^1$H NMR (300 MHz, CDCl$_3$) d 8.85 (d, 1H, J=2.0 Hz), 8.79 (d, 1H, J=2.0 Hz), 8.53 (br s, 1H), 8.16 (t, 1H, J=2.0 Hz), 7.94 (br d, 1H, J=7.8 Hz), 7.60 (dd, 1H, J=2.7, 1.4 Hz), 7.50–7.47 (m, 3H), 7.31 (td, 1H, J=7.6, 1.2 Hz), 7.25 (td, 1H, J=7.8, 1.2 Hz); TLC (40% EtOAc in hexane), R$_f$=0.19; HRMS (electrospray FT/ICR) calcd for C$_{17}$H$_{13}$N$_2$S [M+H]$^+$ 277.0794, found 277.0804.

Example 2

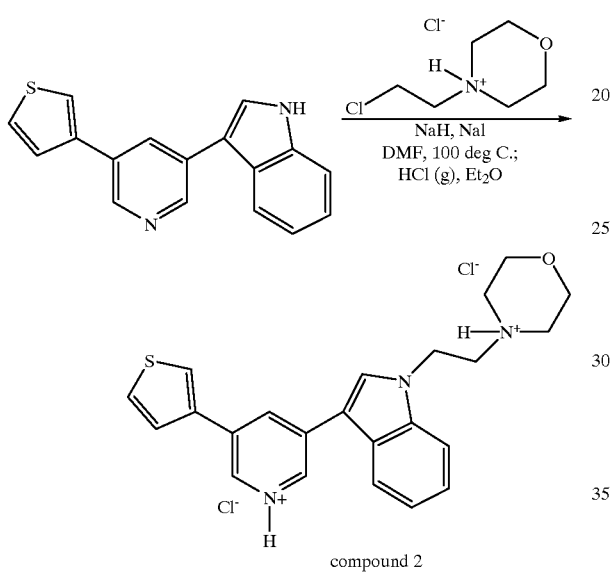

compound 2

95% Sodium hydride (217 mg, 8.60 mmol, 9.50 equiv), 4-(2-chloroethyl)morpholine hydrochloride (202 mg, 1.086 mmol, 1.20 equiv), and sodium iodide (136 mg, 0.905, 1.00 equiv) were sequentially added to a solution of 3-(5-thiophen-3-yl-pyridin-3-yl)-indole (250 mg, 0.905 mmol, 1 equiv) in DMF (60 mL) at 23° C. The resulting mixture was heated at 100° C. for 60 h. The reaction mixture was allowed to cool, then concentrated. The brown-colored residue was partitioned between water (500 ml) and ethyl actetate (3×150 mL). The combined organic extracts were dried over Na$_2$SO$_4$ and concentrated. The residual oil was dissolved in ethyl ether (100 ml), and the resulting solution was subjected to a gentle stream of HCl gas. The precipitate was filtered and washed with ethyl ether (50 ml) to afford compound 2 as a yellow solid.

$^1$H NMR (400 MHz, CD$_3$OD) d 9.14 (t, 1H, J=2.0 Hz), 9.05 (d, 1H, J=2.0 Hz), 9.01 (d, 1H, J=2.0 Hz), 8.28 (dd, 1H, J=2.9, 1.6 Hz), 8.26 (s, 1H), 8.04 (br d, 1H, J=7.6 Hz), 7.78 (dd, 1H, J=5.2, 1.6 Hz), 7.74 (br d, 1H, J=8.1 Hz), 7.72 (dd, 1H, J=5.2, 2.9 Hz), 7.43 (br t, 1H, J=8.1 Hz), 7.36 (br t, 1H, J=7.8 Hz), 4.87 (t, 2H, J=6.7 Hz), 4.05 (br m, 2H), 3.91 (br m, 2H), 3.75 (t, 2H, J=6.7 Hz), 3.58 (br m, 2H), 3.29 (br m, 2H); HRMS (electrospray FT/ICR) calcd for C$_{23}$H$_{24}$N$_3$OS [M+H]$^+$390.1634, found 390.1646; Anal. Calcd for C$_{23}$H$_{23}$N$_3$OS+2.10 HCl+1.30 H2O: C, 56.42; H, 5.70; N, 8.58. Found C, 56.48; H, 5.86; N, 8.22.

Example 3

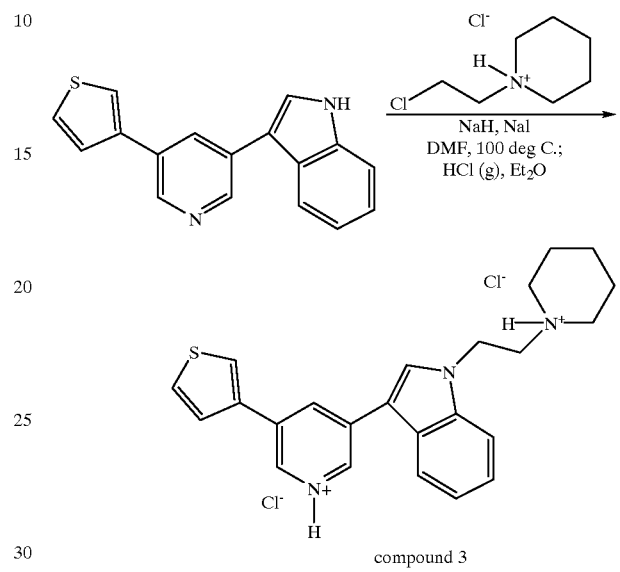

compound 3

95% Sodium hydride (217 mg, 8.60 mmol, 9.50 equiv), 1-(2-chloroethyl)piperidine hydrochloride (200 mg, 1.086 mmol, 1.20 equiv), and sodium iodide (136 mg, 0.905, 1.00 equiv) were sequentially added to a solution of 3-(5-thiophen-3-yl-pyridin-3-yl)-indole (250 mg, 0.905 mmol, 1 equiv) in DMF (60 mL) at 23° C. The resulting mixture was heated at 100° C. for 60 h. The reaction mixture was allowed to cool, then concentrated. The brown-colored residue was partitioned between water (500 ml) and ethyl actetate (3×150 mL). The combined organic extracts were dried over Na$_2$SO$_4$ and concentrated. The residual oil was dissolved in ethyl ether (100 ml), and the resulting solution was subjected to a gentle stream of HCl gas. The precipitate was filtered and washed with ethyl ether (50 ml) to afford compound 3 as a yellow solid.

$^1$H NMR (400 MHz, CD$_3$OD) d 9.13 (t, 1H, J=2.0 Hz), 9.05 (d, 1H, J=2.0 Hz), 9.01 (d, 1H, J=2.0 Hz), 8.28 (dd, 1H, J=2.9, 1.6 Hz), 8.26 (s, 1H), 8.04 (br d, 1H, J=7.6 Hz), 7.78 (dd, 1H, J=5.2, 1.6 Hz), 7.74 (br d, 1H, J=8.1 Hz), 7.72 (dd, 1H, J=5.2, 2.9 Hz), 7.43 (br t, 1H, J=8.1 Hz), 7.36 (br t, 1H, J=7.8 Hz), 4.84 (t, 2H, J=6.7 Hz), 3.67 (t, 2H, J=6.7 Hz), ), 4.05 (br d, 2J=7.3 Hz), 3.08 (br td, 2H, J=6.3, 1.8 Hz), 2.01–1.82 (br m, 5H), 1.54 (m, 1H); HRMS (electrospray FT/ICR) calc'd for C24H26N3S [M+H]$^+$388.1841, found 388.1849; Anal. Calcd for C24H25N3S+2.50 HCl+0.10 ethyl ether: C, 60.28; H, 5.91; N, 8.64. Found C, 59.95; H, 6.22; N, 8.63.

Example 4

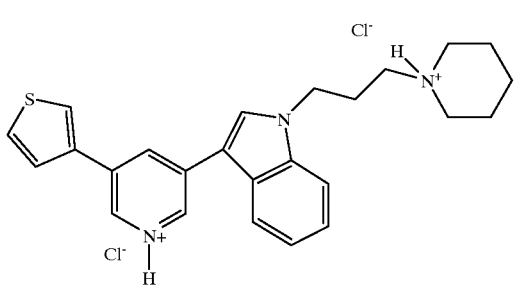

compound 4

3-(5-thiophen-3-yl-pyridin-3-yl)-indole (Compound 1) was prepared by the following alternative reaction sequence for the syntheses of compounds 4–17.

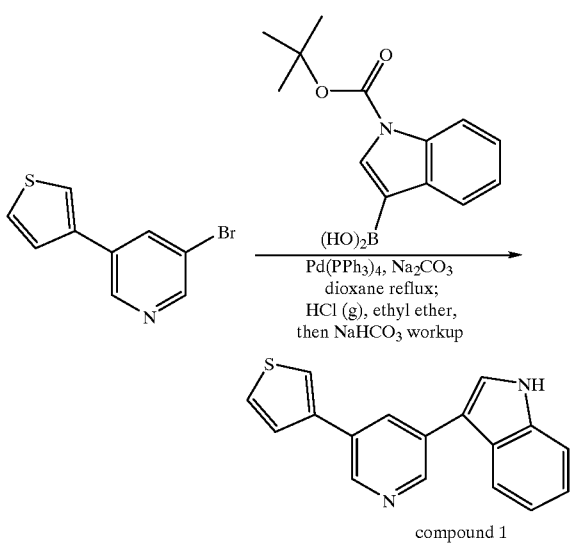

compound 1

A deoxygenated solution of 3-bromo-5-thiophen-3-yl-pyridine (2.50 g, 10.4 mmol, 1 equiv), 1-(t-butyloxycarbonyl)-3-indoleboronic acid (4.073 g, 15.6 mmol, 1.50 equiv), Pd(PPh$_3$)$_4$ (601 mg, 0.520 mmol, 0.0500 equiv), and 2.0 M Na$_2$CO$_3$ (10.4 mL, 20.8 mmol, 2.00 equiv) in dioxane (120 ml) was heated under argon at reflux for 20 h. The reaction mixture was allowed to cool, then partitioned between water (500 mL) and ethyl acetate (3×150 mL). The combined organic layers were washed sequentially with water (500 mL) and brine (500 ml), then dried over sodium sulfate and concentrated. The residue was purified by flash column chromatography (40% ethyl acetate in hexane) to afford 3-(5-thiophen-3-yl-pyridin-3-yl)-1-(t-butyloxycarbonyl)-indole as a colorless oil. The oil was dissolved in ethyl acetate (100 ml), and the resulting solution was cooled to 0° C., then saturated with HCl gas. The solution was allowed to warm to 23° C. and stirred for 30 minutes. The precipitate was filtered and washed with ethyl ether (50 mL). The solid was then partitioned between ethyl acetate (150 mL) and aqueous saturated NaHCO$_3$ solution (150 mL). The organic layer was dried over Na$_2$SO$_4$ and concentrated to give compound 1 (3-(5-thiophen-3-yl-pyridin-3-yl)-indole) as a white solid.

$^1$H NMR (300 MHz, CDCl$_3$) d 8.86 (d, 1H, J=2.0 Hz), 8.77 (d, 1H, J=2.2 Hz), 8.09 (br d, 1H, J=8.1 Hz), 8.06 (t, 1H, J=2.2 Hz), 7.84 (d, 2H, J=8.5 Hz), 7.80 (s, 1H), 7.76 (br d, 1H, J=7.8 Hz), 7.59 (dd, 1H, J=2.7, 1.2 Hz), 7.48 (dd, 1H, J=5.1, 2.9 Hz), 7.44 (dd, 1H, J=5.1, 1.2 Hz), 7.41 (br t, J=7.3 Hz), 7.32 (br t, 1H, J=7.6 Hz), 7.26 (d, 2H, J=8.0 Hz), 2.36 (s, 3H); TLC (40% EtOAc in hexane), R$_f$=0.26.

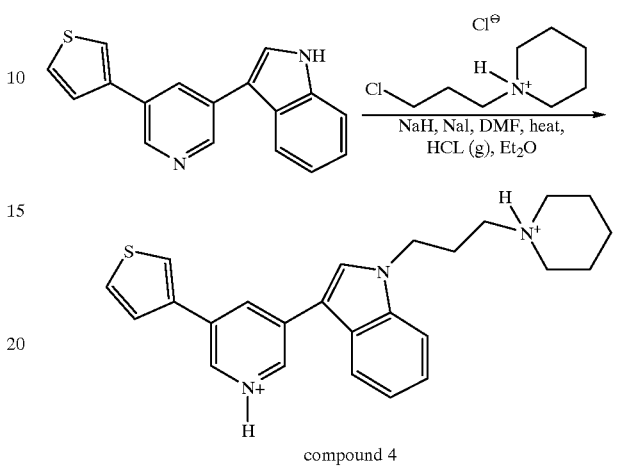

compound 4

95% Sodium hydride (217 mg, 8.60 mmol, 9.50 equiv), 1-(2-chloropropyl)piperidine hydrochloride (200 mg, 1.086 mmol, 1.20 equiv), and sodium iodide (136 mg, 0.905, 1.00 equiv) were sequentially added to a solution of 3-(5-thiophen-3-yl-pyridin-3-yl)-indole (250 mg, 0.905 mmol, 1 equiv) in DMF (50 mL) at 23° C. The resulting mixture was heated at 100° C. for 60 h. The reaction mixture was allowed to cool, then concentrated. The brown-colored residue was partitioned between water (500 ml) and ethyl actetate (3×150 mL). The combined organic extracts were washed with brine (500 mL) then dried over Na$_2$SO$_4$ and concentrated. The residual oil was dissolved in ethyl ether (100 ml), and the resulting solution was subjected to a gentle stream of HCl gas. The precipitate was filtered and washed with ethyl ether (50 ml) to afford compound 4 as a yellow solid.

$^1$H NMR (300 MHz, CD$_3$OD) d 9.13 (t, 1H, J=2.0 Hz), 9.05 (d, 1H, J=2.0 Hz), 8.98 (d, 1H, J=2.0 Hz), 8.29 (dd, 1H, J=2.9, 1.5 Hz), 8.23 (s, 1H), 8.03 (br d, 1H, J=7.3 Hz), 7.78 (dd, 1H, J=5.1, 1.5 Hz), 7.72 (dd, 1H, J=5.1, 2.9 Hz), 7.66 (br d, 1H, J=8.1 Hz), 7.39 (br td, 1H, J=7.6, 1.2 Hz), 7.32 (br td, 1H, J=8.1, 1.5 Hz), 4.46 (t, 2H, J=6.8 Hz), 3.52 (br d, 2H, J=12.5 Hz), 3.17 (m, 2H), 2.92 (br td, 2H, J=12.9, 2.8 Hz), 2.43 (m, 2H), 1.98–1.70 (br m, 5H), 1.50 (m, 1H); HRMS (electrospray FT/ICR) calcd for C25H28N3S [M+H]$^+$ 402.1998, found 402.2013; Anal. Calcd for C$_{25}$H$_{27}$N$_3$S+ 2.50 HCl+0.40 H$_2$O: C, 60.06; H, 6.11; N, 8.41. Found C, 60.10; H, 6.19; N, 8.07.

Example 5–17

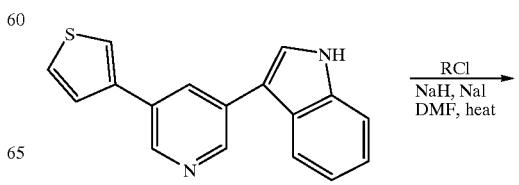

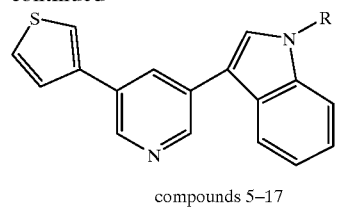

compounds 5–17

A general experimental procedure for the preparation of compounds 5–17 is given below. The product mass spectral data are summarized in Table 1 below.

95% Sodium hydride (21.7 mg, 0.860 mmol, 9.50 equiv), the appropriate alkyl chloride (0.109 mmol, 1.20 equiv), and sodium iodide (13.6 mg, 0.0905, 1.00 equiv) were sequentially added to a solution of 3-(5-thiophen-3-yl-pyridin-3-yl)-indole (25.0 mg, 0.0905 mmol, 1 equiv) in DMF 5 (1 mL) at 23° C. The resulting mixture was heated at 100° C. for 20 h. The reaction mixture was allowed to cool, then concentrated. The browncolored residue was partitioned between water (3 ml) and ethyl actetate (3×3 mL). The combined organic extracts were dried over $Na_2SO_4$ and concentrated to afford the desired product as yellow oil. Compounds 7, 8, and 15 were purified by flash column chromatography (10–20% MeOH in $CH_2Cl_2$).

TABLE 1

| Cmpd | Structure | RCl | Calcd Mass [M + H]+ | Found Mass (FAB+) |
|---|---|---|---|---|
| 5 | 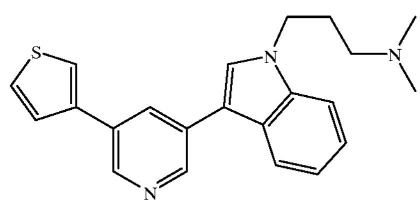 | | $C_{22}H_{24}N_3S$ = 362.17 | 362.17 |
| 6 | 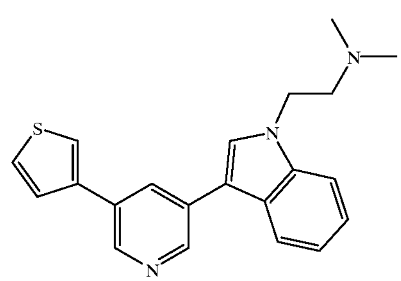 | | $C_{21}H_{22}N_3S$ = 348.15 | 348.15 |
| 7 | 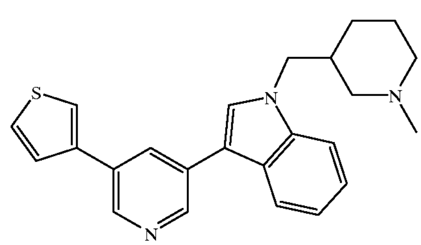 | | $C_{24}H_{26}N_3S$ = 388.18 | 388.18 |
| 8 | 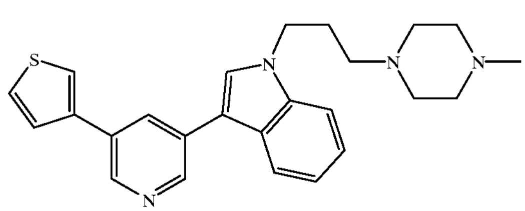 | | $C_{25}H_{29}N_3S$ = 417.21 | 417.20 |

TABLE 1-continued

| Cmpd | Structure | RCl | Calcd Mass [M + H]+ | Found Mass (FAB+) |
|---|---|---|---|---|
| 9 | 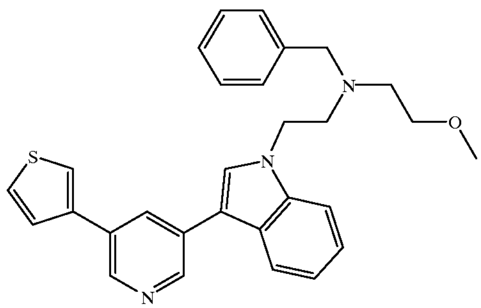 | | C29H30N3OS = 468.21 | 468.21 |
| 10 | 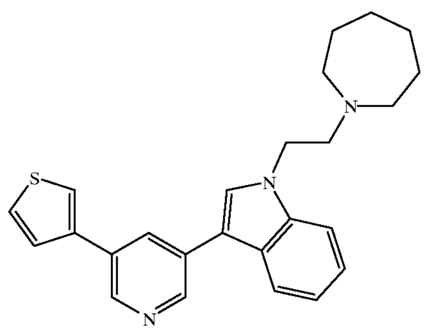 | | C25H28N3S = 402.20 | 402.20 |
| 11 | 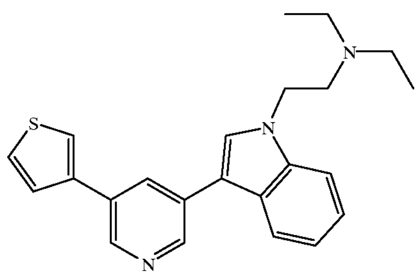 | | C23H26N3S = 376.18 | 376.18 |
| 12 | 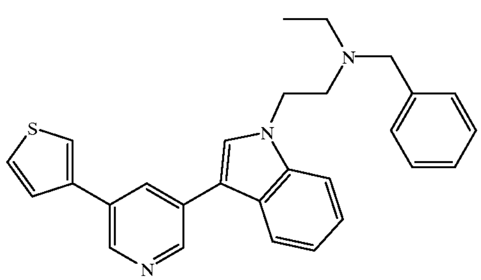 | | C28H28N3S = 438.20 | 438.20 |
| 13 | 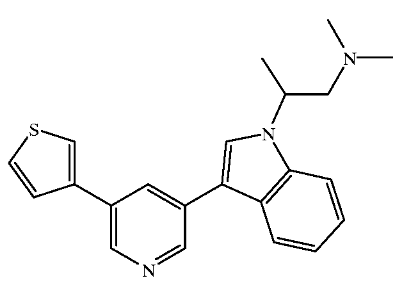 | | C22H24N3S = 362.17 | 362.17 |

TABLE 1-continued

| Cmpd | Structure | RCl | Calcd Mass [M + H]$^+$ | Found Mass (FAB$^+$) |
|------|-----------|-----|------------------------|----------------------|
| 14 | 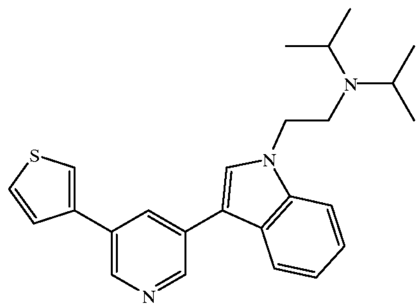 | | $C_{25}H_{30}N_3S$ = 404.22 | 404.21 |
| 15 | 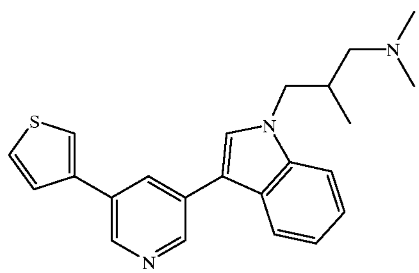 | | $C_{23}H_{26}N_3S$ = 376.18 | 376.18 |
| 16 | 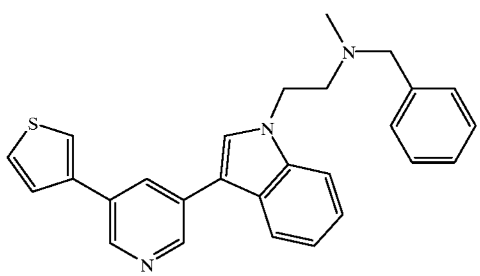 | | $C_{27}H_{26}N_3S$ = 424.18 | 424.19 |
| 17 | 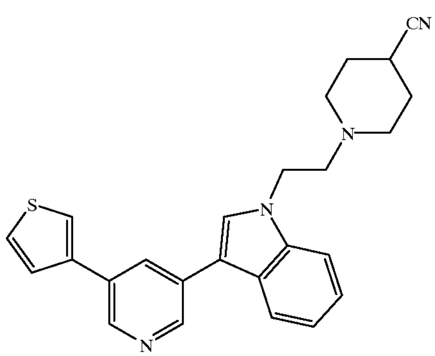 | | $C_{25}H_{25}N_3S$ = 413.18 | 413.18 |

*After purification by flash column chromatography (10–20% MeOH in $CH_2Cl_2$)

The activity of the disclosed compounds as kinase inhibitors was demonstrated in accordance with the following protocols.

VEGF RECEPTOR KINASE ASSAY

VEGF receptor kinase activity is measured by incorporation of radio-labeled phosphate into polyglutamic acid, tyrosine, 4:1 (pEY) substrate. The phosphorylated pEY product is trapped onto a filter membrane and the incoporation of radio-labeled phosphate quantified by scintillation counting.

MATERIALS

VEGF Receptor Kinase

The intracellular tyrosine kinase domains of human KDR (Terman, B.I. et al. Oncogene (1991) vol. 6, pp. 1677–1683.) and Flt-1 (Shibuya, M. et al. Oncogene (1990) vol. 5, pp. 519–524) were cloned as glutathione S-transferase (GST) gene fusion proteins. This was accomplished by cloning the cytoplasmic domain of the KDR kinase as an in frame fusion at the carboxy terminus of the GST gene. Soluble recombinant GST-kinase domain fusion proteins were expressed in Spodoptera frugiperda (Sf21) insect cells (Invitrogen) using a baculovirus expression vector (pAcG2T, Pharmingen).

Lysis Buffer 50 mM Tris pH 7.4, 0.5 M NaCl, 5 mM DTT, 1 mM EDTA, 0.5% triton X-100, 10% glycerol, 10 mg/ml of each leupeptin, pepstatin and aprotinin and 1 mM phenylmethylsulfonyl fluoride (all Sigma).

Wash Buffer 50 mM Tris pH 7.4, 0.5 M NaCl, 5 mM DTT, 1 mM EDTA, 0.05% triton X-100, 10% glycerol, 10 mg/ml of each leupeptin, pepstatin and aprotinin and 1 mM phenylmethylsulfonyl fluoride.

Dialysis Buffer 50 mM Tris pH 7.4, 0.5 M NaCl, 5 mM DTT, 1 mM EDTA, 0.05% triton X-100, 50% glycerol, 10 mg/ml of each leupeptin, pepstatin and aprotinin and 1 mM phenylmethylsuflonyl fluoride 10X Reaction Buffer 200 mM Tris, pH 7.4, 1.0 M NaCl, 50 mM $MnCl_2$, 10 mM DTT and 5 mg/ml bovine serum albumin (Sigma).

Enzyme Dilution Buffer 50 mM Tris, pH 7.4, 0.1 M NaCl, 1 mM DTT, 10% glycerol, 100 mg/ml BSA.

10X Substrate

750 µg/ml poly (glutamic acid, tyrosine; 4:1) (Sigma).

Stop Solution

30% trichloroacetic acid, 0.2 M sodium pyrophosphate (both Fisher).

Wash Solution

15% trichloroacetic acid, 0.2 M sodium pyrophosphate.

Filter Plates

Millipore #MAFC NOB, GF/C glass fiber 96 well plate.

METHOD

A. Protein Purification

1. Sf21 cells were infected with recombinant virus at a multiplicity of infection of 5 virus particles/ cell and grown at 27° C. for 48 hours.

2. All steps were performed at 4° C. Infected cells were harvested by centrifugation at 1000×g and lysed at 4° C. for 30 minutes with 1/10 volume of lysis buffer followed by centrifugation at 100,000×g for 1 hour. The supernatant was then passed over a glutathione Sepharose column (Pharmacia) equilibrated in lysis buffer and washed with 5 volumes of the same buffer followed by 5 volumes of wash buffer. Recombinant GST-KDR protein was eluted with wash buffer/10 mM reduced glutathione (Sigma) and dialyzed against dialysis buffer.

B. VEGF Receptor Kinase Assay

1. Add 5 µl of inhibitor or control to the assay in 50% DMSO.

2. Add 35 µl of reaction mix containing 5 µl of 10×reaction buffer, 5 µl 25 mM ATP/10 µCi [$^{33}$P]ATP (Amersham), and 5 µl of 10×substrate.

3. Start the reaction by the addition of 10 gl of KDR (25 nM) in enzyme dilution buffer.

4. Mix and incubate at room temperature for 15 minutes.

5. Stop by the addition of 50 µl stop solution.

6. Incubate for 15 minutes at 4° C.

7. Transfer a 90 µl aliquot to filter plate.

8. Aspirate and wash 3 times with wash solution.

9. Add 30 µl of scintillation cocktail, seal plate and count in a Wallac Microbeta scintillation counter.

Human Umbilical Vein Endothelial Cell Mitogenesis Assay

Expression of VEGF receptors that mediate mitogenic responses to the growth factor is largely restricted to vascular endothelial cells. Human umbilical vein endothelial cells (HUVECs) in culture proliferate in response to VEGF treatment and can be used as an assay system to quantify the effects of KDR kinase inhibitors on VEGF stimulation. In the assay described, quiescent HUVEC monolayers are treated with vehicle or test compound 2 hours prior to addition of VEGF or basic fibroblast growth factor (bFGF). The mitogenic response to VEGF or bFGF is determined by measuring the incorporation of [$^3$H] thymidine into cellular DNA.

Materials

HUVECs

HUVECs frozen as primary culture isolates are obtained from Clonetics Corp. Cells are maintained in Endothelial Growth Medium (EGM; Clonetics) and are used for mitogenic assays at passages 3–7.

Culture Plates

NUNCLON 96-well polystyrene tissue culture plates (NUNC #167008).

Assay Medium

Dulbecco's modification of Eagle's medium containing 1 g/ml glucose (low-glucose DMEM; Mediatech) plus 10% (v/v) fetal bovine serum (Clonetics).

Test Compounds

Working stocks of test compounds are diluted serially in 100% dimethylsulfoxide (DMSO) to 400-fold greater than their desired final concentrations. Final dilutions to 1X concentration are made directly into Assay Medium immediately prior to addition to cells.

10X Growth Factors

Solutions of human $VEGF_{165}$ (500 ng/ml; R&D Systems) and bFGF (10 ng/ml; R&D Systems) are prepared in Assay Medium.

10X [$^3$]Thymidine

[Methyl-$^3$H]Thymidine (20 Ci/mmol; Dupont-NEN) is diluted to 80 uCi/ml in low-glucose DMEM.

Cell Wash Medium

Hank's balanced salt solution (Mediatech) containing 1 mg/ml bovine serum albumin (Boehringer-Mannheim).

Cell Lysis Solution

1 N NaOH, 2% (w/v) $Na_2CO_3$.

Method

1. HUVEC monolayers maintained in EGM are harvested by trypsinization and plated at a density of 4000 cells per 100 ul Assay Medium per well in 96-well plates. Cells are growth-arrested for 24 hours at 37° C. in a humidified atmosphere containing 5% $CO_2$.

2. Growth-arrest medium is replaced by 100 ul Assay Medium containing either vehicle (0.25% [v/v] DMSO) or the desired final concentration of test compound. All determinations are performed in triplicate. Cells are then incubated at 37° C./5% $CO_2$ for 2 hours to allow test compounds to enter cells.

3. After the 2-hour pretreatment period, cells are stimulated by addition of 10 ul/well of either Assay Medium, 10X VEGF solution or 10X bFGF solution. Cells are then incubated at 37° C./5% $CO_2$.

4. After 24 hours in the presence of growth factors, 10X [$^3$H]Thymidine (10 ul/well) is added.

5. Three days after addition of [$^3$H]thymidine, medium is removed by aspiration, and cells are washed twice with Cell Wash Medium (400 ul/well followed by 200 ul/well). The washed, adherent cells are then solubilized by addition of Cell Lysis Solution (100 ul/well) and warming to 37° C. for 30 minutes. Cell lysates are transferred to 7-ml glass scintillation vials containing 150 ul of water. Scintillation cocktail (5 ml/vial) is added, and cell-associated radioactivity is determined by liquid scintillation spectroscopy.

Based upon the foregoing assays the compounds of formula I are inhibitors of VEGF and thus are useful for the inhibition of neoangiogenesis, such as in the treatment of occular disease, e.g., diabetic retinopathy and in the treatment of cancers, e.g., solid tumors. The instant compounds inhibit VEGF-stimulated mitogenesis of human vascular endothelial cells in culture with $IC_{50}$ values between 0.01–5.0 µM. These compounds also show selectivity over related tyrosine kinases (e.g. FGFR1 and the Src family).

What is claimed is:

1. A compound in accordance with formula I:

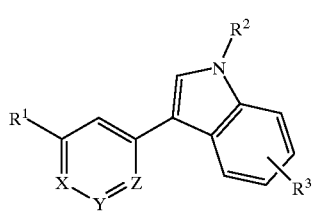

or a pharmaceutically acceptable salt or hydrate thereof, wherein

X—Y=Z is N—CH=CH, CH—N=CH, or CH—CH=N;

$R^1$ is thienyl or phenyl, said thienyl and phenyl optionally substituted with one to three substituents selected from halogen, $O(C_{1-6})$alkyl, $(C_{1-6})$alkyl, and OH;

$R^2$ is $C_{1-6}$ alkyl-$NR^7R^8$ or $C_{1-6}$ alkyl-heterocyclyl, wherein the heterocyclyl is piperidinyl, piperazinyl, azepinyl or morpholinyl and optionally substituted with CN, halo, or $C_{1-6}$ alkyl;

$R^3$ is H, halogen, CN, $O(C_{1-6})$alkyl, $(C_{1-6})$alkyl, $CO_2R$, —$C_{1-6}$ alkylene-$CO_2R$, or —$C_{1-6}$ alkylene-O—$C_{1-6}$ alkyl;

R is H or $C_{1-6}$ alkyl; and $R^7$ and $R^8$ are independently H, $C_{1-10}$ alkyl, $C_{3-6}$ cycloalkyl, COR, —$C_{1-6}$ alkylene-O—$C_{1-6}$ alkyl, —$C_{1-6}$ alkylene-aryl, COOR, aryl, benzyl, or $NR^7R^8$ are taken together to form a 5–7 membered heterocyclic ring optionally containing, in addition to the nitrogen atom attached to $R^7$ and $R^8$, one or two non-adjacent additional hetero-atoms selected from N, O, and S, and optionally substituted with CN, halo, or $C_{1-6}$ alkyl.

2. A compound according to claim 1 wherein X—Y=Z is CH—N=CH.

3. A compound selected from the group consisting of:

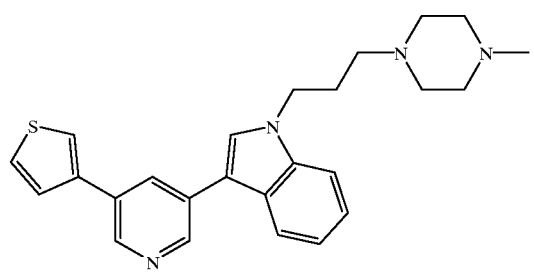

1-[3-(4-methyl-piperazin-1-yl)-propyl]-3-(5-thiophen-3-yl-pyridin-3-yl)-1H-indole;

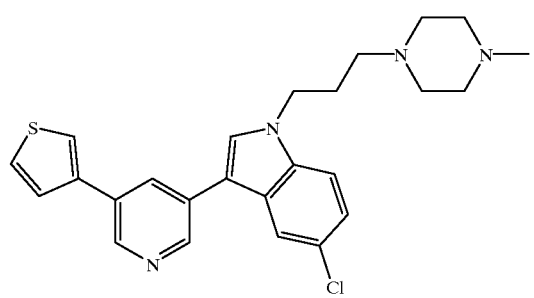

5-chloro-1-[3-(4-methyl-piperazin-1-yl)-propyl]3-(5-thiophen-3-yl-pyridin-3-yl)-1H-indole;

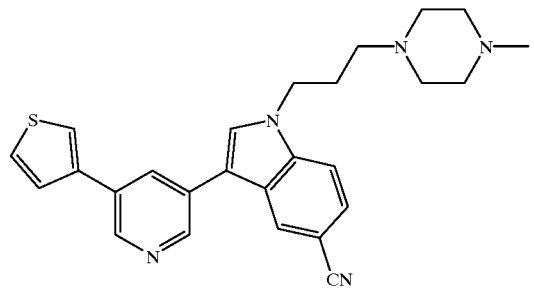

1-[3-(4-methyl-piperazin-1-yl)-propyl]-3-(5-thiophen-3-yl-yl-pyridin-3-yl)-1-H-indole-5-carbonitrile;

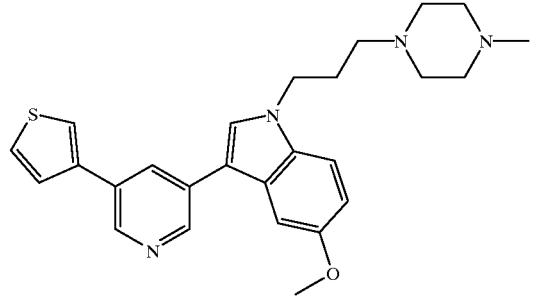

5-methoxy-1-[3-(4-methyl-piperazin-1-yl)-propyl]-3-(5-thiophen-3-yl-pyridin-3-yl)-1H-indole;
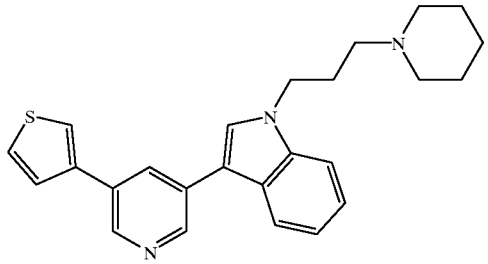
1-(3-piperidin-1-yl-propyl-3-(5-thiophen-3-yl-pyridin-3-yl)-1H-indole; and
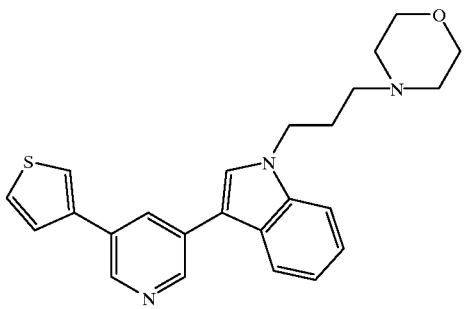
1-(2-morpholin-4-yl-ethyl)-3-(5-thiophen-3-yl-pyridin-3-yl)-1H-indole; or a pharmaceutically acceptable salt thereof.
4. A pharmaceutical composition which is comprised of a compound in accordance with claim 1 and a pharmaceutically acceptable carrier.
* * * * *